(12) United States Patent
Field et al.

(10) Patent No.: US 11,510,661 B2
(45) Date of Patent: Nov. 29, 2022

(54) FULL CORE BIOPSY DEVICE

(71) Applicant: RLS INTERVENTIONAL, INC., Grand Rapids, MI (US)

(72) Inventors: Steven E. Field, Grand Rapids, MI (US); Chad J. Bacon, Coopersville, MI (US)

(73) Assignee: RLS Interventional, Inc., Grand Rapids, MI (US)

( * ) Notice: Subject to any disclaimer, the term of this patent is extended or adjusted under 35 U.S.C. 154(b) by 887 days.

(21) Appl. No.: 16/263,990

(22) Filed: Jan. 31, 2019

(65) Prior Publication Data
US 2019/0247029 A1 Aug. 15, 2019

Related U.S. Application Data

(60) Provisional application No. 62/630,960, filed on Feb. 15, 2018.

(51) Int. Cl.
*A61B 10/02* (2006.01)
*A61B 17/3205* (2006.01)
*A61B 17/34* (2006.01)

(52) U.S. Cl.
CPC ...... *A61B 10/0275* (2013.01); *A61B 10/0266* (2013.01); *A61B 17/32053* (2013.01); *A61B 17/3421* (2013.01); *A61B 2010/0208* (2013.01)

(58) Field of Classification Search
CPC ............ A61B 10/0275; A61B 10/0266; A61B 17/32053; A61B 17/3421; A61B 2010/0208
See application file for complete search history.

(56) References Cited

U.S. PATENT DOCUMENTS

| | | | |
|---|---|---|---|
| 5,655,542 A | 8/1997 | Weilandt | |
| 6,126,617 A | 10/2000 | Weilandt et al. | |
| 6,551,254 B2 | 4/2003 | Nishtalas et al. | |
| 7,608,048 B2 | 10/2009 | Goldenberg | |
| 7,635,340 B2 | 12/2009 | Vetter et al. | |
| 8,088,081 B2 | 1/2012 | Field et al. | |
| 8,192,369 B2 | 6/2012 | Bacon et al. | |
| 8,197,419 B2 | 6/2012 | Field et al. | |
| 8,475,393 B1 | 7/2013 | Hameed et al. | |
| 8,568,334 B2 | 10/2013 | Field et al. | |
| 2006/0030785 A1* | 2/2006 | Field | A61B 10/0275 600/567 |
| 2006/0116605 A1* | 6/2006 | Nakao | A61B 10/0266 600/566 |
| 2008/0281226 A1 | 11/2008 | Peters | |
| 2009/0012423 A1* | 1/2009 | Peters | A61B 10/0266 600/567 |
| 2009/0299220 A1 | 12/2009 | Field et al. | |

(Continued)

OTHER PUBLICATIONS

European Search Report for Counterpart EP19156313.9, dated Jun. 13, 2019.

*Primary Examiner* — Sean P Dougherty
(74) *Attorney, Agent, or Firm* — McGarry Bair PC

(57) ABSTRACT

A full core biopsy device includes a needle assembly having stylet, spoon, and at least one coring cannula. A window is located in at least one of the spoon and coring cannula. A excising finger is configured to prolapse through the window into a lumen of the inner spoon or cannula to sever a tissue sample upon translation or axial advancement of the excising finger.

43 Claims, 18 Drawing Sheets

(56) References Cited

U.S. PATENT DOCUMENTS

| | | | |
|---|---|---|---|
| 2009/0299221 A1* | 12/2009 | Bacon | A61B 10/0275 600/567 |
| 2014/0171826 A1 | 6/2014 | Lampropoulos et al. | |
| 2016/0089208 A1 | 3/2016 | Vetter | |
| 2016/0192961 A1* | 7/2016 | Ginggen | A61B 17/14 604/173 |
| 2019/0247029 A1* | 8/2019 | Field | A61B 17/32053 |

* cited by examiner

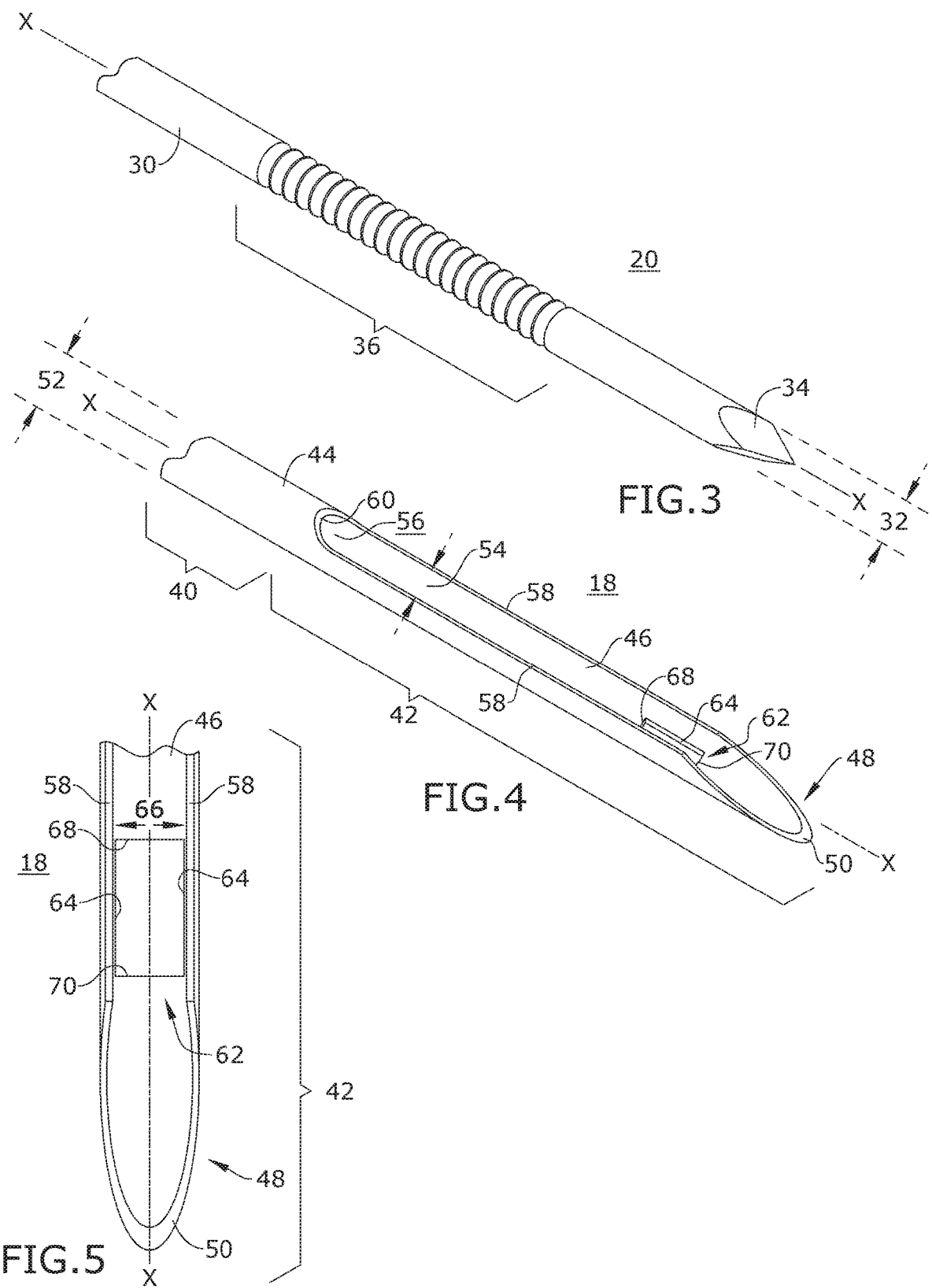

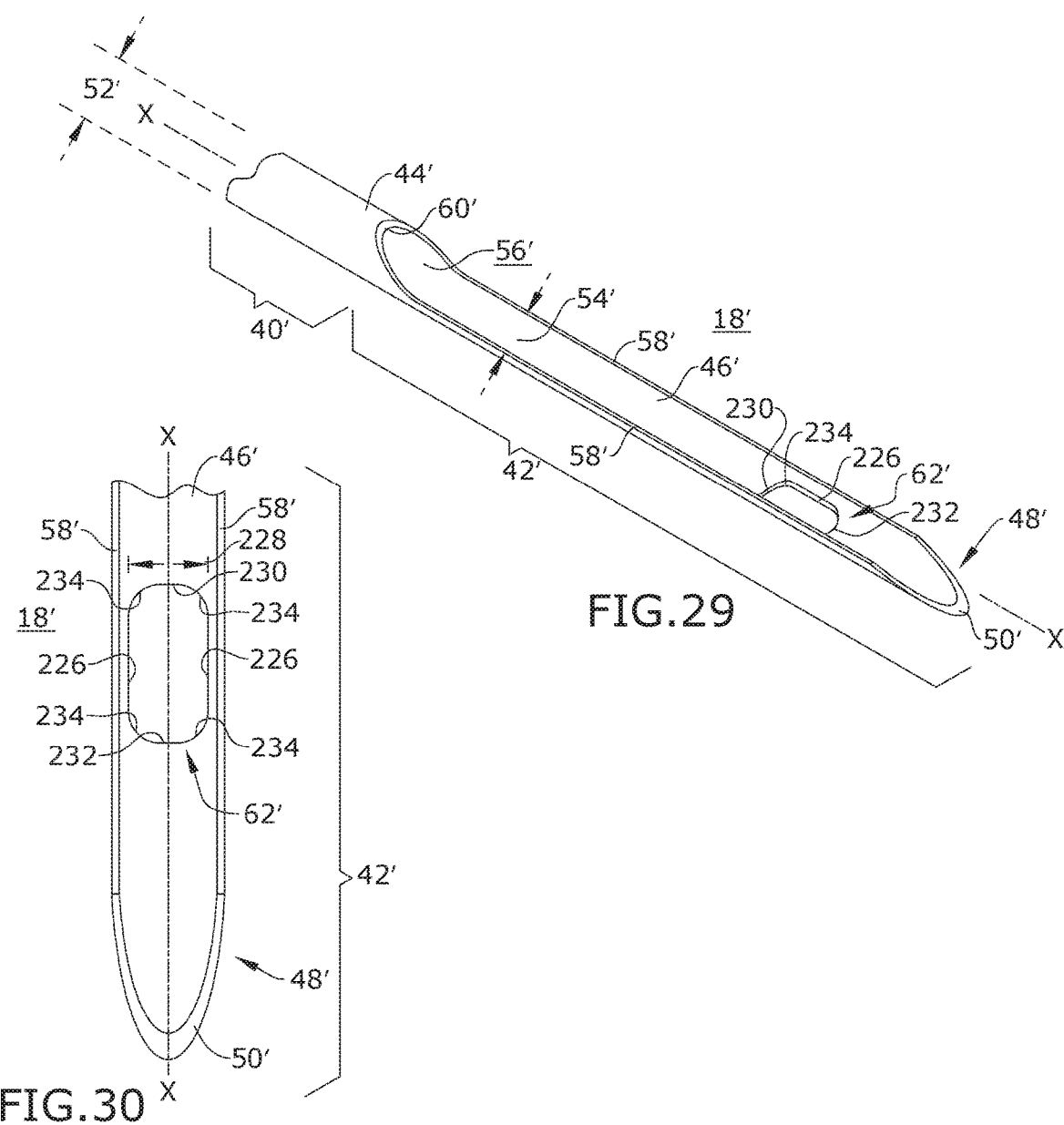
FIG.29
FIG.30
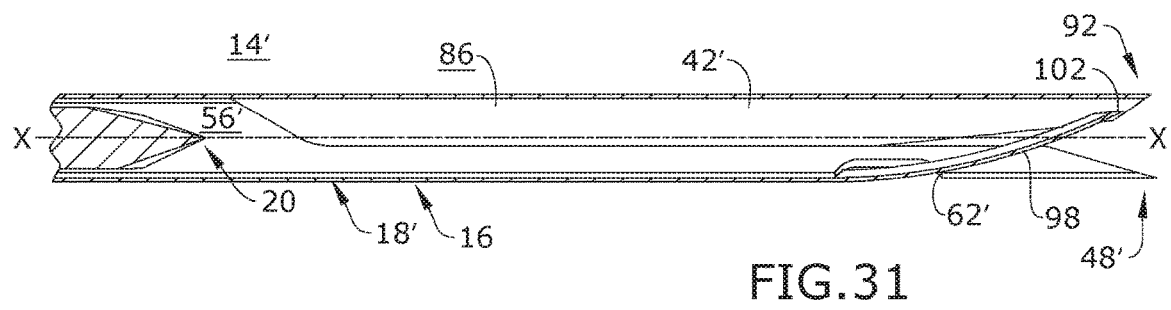
FIG.31

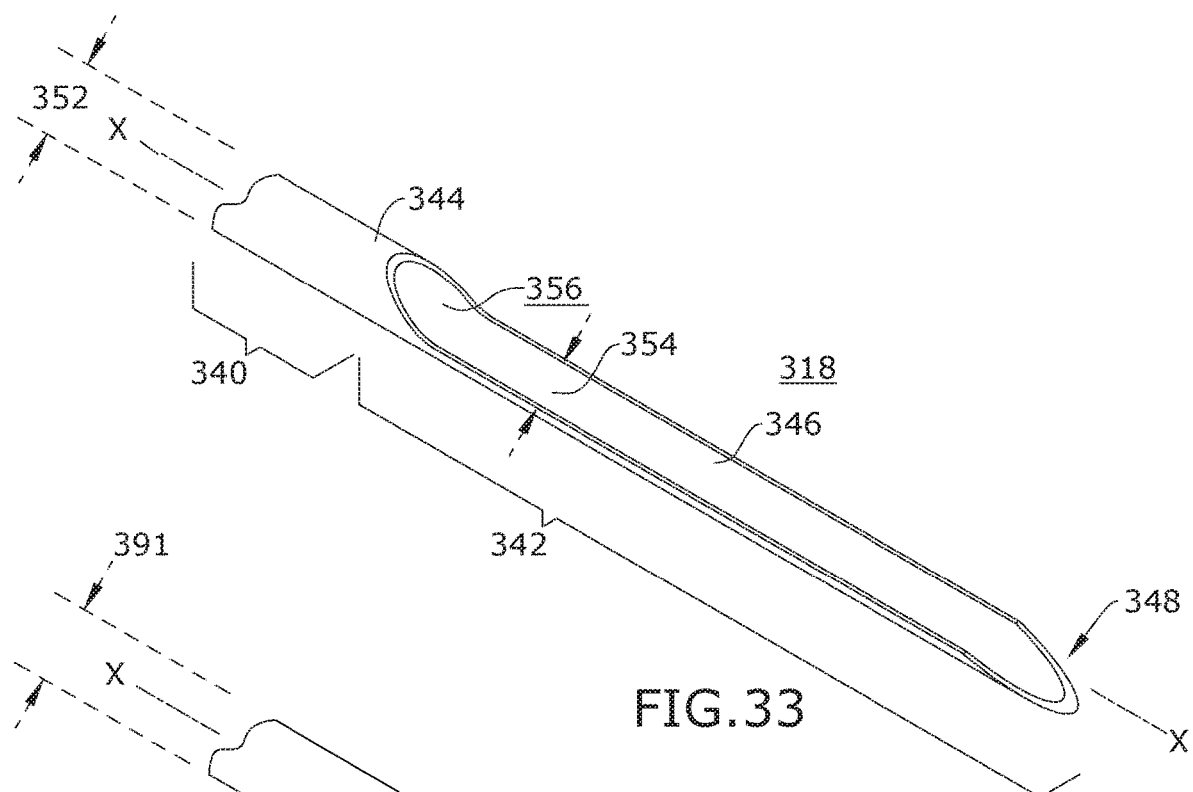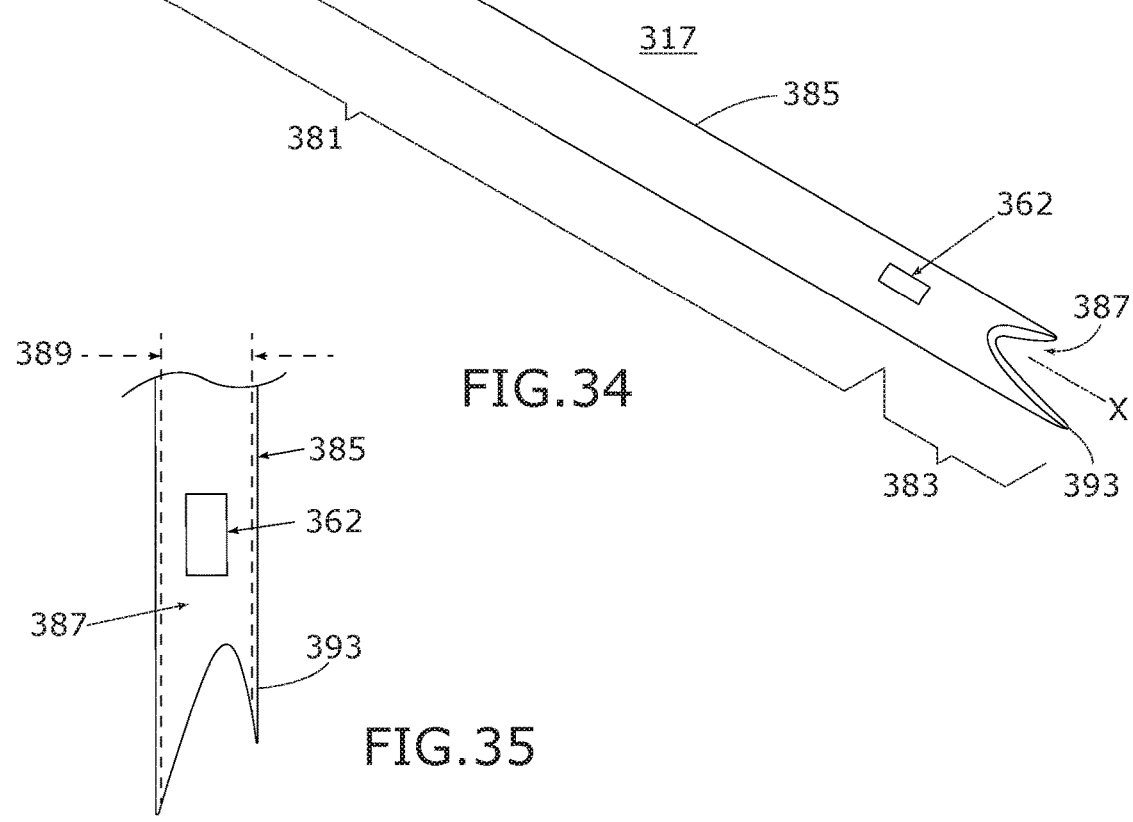

FULL CORE BIOPSY DEVICE

CROSS-REFERENCE TO RELATED APPLICATION(S)

This application claims priority to U.S. Provisional Patent Application No. 62/630,960, filed Feb. 15, 2018, which is incorporated herein by reference in its entirety.

BACKGROUND

It is frequently necessary to sample or remove a sample from a suspect tissue for testing. In humans, such a sample removal is particularly useful in the diagnosis and treatment of cancerous or pre-cancerous conditions. In the case of suspected cancer, particularly cancer of the breast, early detection and diagnosis is critical to the success of the patient's treatment and recovery.

Various techniques are available to aid in detection and diagnosis, including physical examination and imaging, such as mammography, x-ray, ultrasound, magnetic resonance imaging (MRI), and the like. When a condition is detected that suggests the possibility of cancer, a biopsy can be performed to obtain tissue samples for a complete diagnosis.

One biopsy technique frequently performed is a core biopsy, which uses a core biopsy device in which a cannula is inserted into the tissue of interest, thereby coring a biopsy sample from the tissue having a cross section similar to that of the cannula, and which is retained within the cannula. The cannula, with the biopsy sample, is then removed from the tissue, followed by cytological and/or histological analysis of the sample.

One group of core biopsy devices is based on the combination of a notched inner stylet and an outer severing cannula. The stylet is retained within the lumen of the outer cannula such that the pointed end of the stylet closes off the open end of the cannula. The stylet and cannula are advanced into the tissue mass until they are near the desired biopsy site. The stylet is then advanced relative to the outer cannula to expose the notch to the biopsy site where the tissue prolapses into the notch. The outer cannula is then advanced to sever the tissue in the notch. The disadvantage of this method is that it produces a small core biopsy, referred to as a "partial core" biopsy, relative to the outer cannula size since the cross section of the sample is substantially equal to the cross section of the stylet notch, which is substantially smaller than the cross section of the outer cannula. The advantage of this method is that the sample is completely severed from the tissue mass and securely retained within the notch.

Another group of core biopsy devices is based on a coring cannula in combination with a non-notched stylet. The stylet is used to plug the end of the coring cannula during the insertion of the coring cannula into the tissue adjacent the biopsy site. The coring cannula is then advanced relative to the stylet into the biopsy site to retain a sample within the coring cannula. The advantage of this device is that a full core biopsy sample is obtained. That is, the "full core" sample has a cross section that is substantially equal to the cross section of the coring cannula. The full core sample provides a much larger sample which is highly advantageous.

The disadvantage of this full core device is that the end of the sample is not positively severed from the tissue mass, creating the possibility that the biopsy sample will be pulled out of the coring cannula upon the withdrawal of the coring cannula. This can happen if the forces holding the sample in the coring cannula are not sufficient to tear the end of the sample from the tissue mass. Since the sample normally comprises wetted tissue that completely fills the coring cannula, the suction force and/or the frictional force between the tissue sample and the inner wall of the coring cannula are the dominate forces for retaining the sample in the cannula. However, if these forces are not sufficient to tear the end of the sample from the tissue mass, the sample will be pulled out of the coring cannula upon the removal of the coring cannula. Some practitioners pivot the biopsy device in hopes that the end of the cannula will at least partially sever the attached portion of the sample. However, this is not preferred as it increases the damage to the remaining tissue.

Attempts have been made to improve the severing of the sample from the tissue mass for the full core device. In some cases, the interior of the coring cannula is provided with a raceway in which a severing finger could be advanced/retracted. After the advancing of the cannula to take the core sample, the severing finger is advanced, guided by the raceway, to sever the tissue. In some cases, when the finger is advanced, it closes the end of the coring cannula and is left in the advanced position during removal. A disadvantage of this method is that the sample is not truly a full core sample since part of the interior of the cannula was reserved for the raceway. If the sample produced by the cannula with the raceway was the same size as the full core sample, the cannula with the raceway would require a larger cross sectional cannula, which is not desirable. In the biopsy art, it is highly desirable to minimize the cross section of the cannula to minimize the damage to the surrounding tissue and to minimize the invasiveness of the procedure. Generally, the smaller the cross section, the less pain the patient experiences after the procedure, and the more desirable the device.

Another alternative to severing the sample end in a full core device comprises the addition of a cutting cannula that circumscribes the coring cannula. The cutting cannula has a cutting element that severs the sample within the coring cannula or at the tip of the coring cannula.

Another disadvantage of some full core devices is that they rely on the relative movement between the coring cannula and the stylet to expel the sample from the interior of the coring cannula. The use of the stylet to force out the sample can damage the sample. The damage can be great enough to render the sample unsuitable for testing. This can be very detrimental since some lesions being sampled are small enough that the entire lesion is contained within the sample. For larger lesions, some practitioners will take multiple samples to allow for potential damage of one of the samples. This practice increases the invasiveness of the procedure and the pain to the patient.

BRIEF SUMMARY

A biopsy device comprising an operationally stationary stylet terminating in a penetration tip; a spoon cannula having an annular wall forming an enclosed section defining a first lumen in which the stylet is received, and a spoon having a first arcuate wall contiguous with and extending from a portion of the annular wall, the first arcuate wall having spaced first edges defining a specimen opening and terminating in a spoon tip, and a window is located in the arcuate wall; a coring cannula having an enclosed section defining a second lumen in which the spoon cannula is received, and a cutting section extending distally from the enclosed section, the cutting section having a second arcuate wall having spaced second edges and terminating in a coring tip, and with an excising finger spaced from the second arcuate wall; and an actuator assembly operably coupled to the spoon cannula and the coring cannula to effect movement of the spoon cannula and coring cannula from an armed position to a fired position to take a tissue specimen from a tissue mass, in the armed position, at least the stylet and spoon are arranged such that the stylet resides within the spoon, in the fired position, the stylet, spoon and cutting section are arranged such that the spoon extends beyond the penetration tip of the stylet, the second arcuate wall closes at least a portion of the specimen opening, and the excising finger extends through the window.

A method of operating a biopsy device to take a tissue sample, the method comprising: advancing, without rotation, a spoon cannula beyond a tip of a stylet and into a tissue mass to partially sever a portion of the tissue mass within a spoon of the spoon cannula to form a partial specimen core; advancing a coring cannula over the spoon cannula to sever a portion of the tissue mass above the spoon to form a complete specimen core; and advancing, without rotation, an excising finger carried by the coring cannula through a window in spoon cannula to sever a distal end of the specimen core from the tissue mass.

A biopsy device comprising: a stylet terminating in a penetration tip; a spoon cannula having an annular wall forming an enclosed section defining a spoon lumen in which the stylet is received, and a spoon having a spoon arcuate wall contiguous with and extending from a portion of the annular wall, the spoon arcuate wall having spaced spoon edges defining a specimen opening and terminating in a spoon tip; a first coring cannula defining a first coring cannula lumen and terminating in a first coring tip; a second coring cannula defining a second coring lumen and terminating in a second coring tip, with the spoon cannula, first coring cannula, and second coring all coaxially arranged; a window located in one of the first and second coring cannulas; an excising finger spaced extending from another one of the first and second coring cannulas; and an actuator assembly operably coupled to the stylet, spoon cannula, first coring cannula and second coring cannula to effect movement of the spoon cannula, first coring cannula, and second coring cannula from an armed position to a fired position to take a tissue specimen from a tissue mass, in the armed position, at least the penetration tip extends beyond the spoon tip, and, in the fired position, the spoon tip extends beyond the penetration tip, at least one of the first and second cannulas closes a portion of the specimen opening, and the excising finger extends through the window.

BRIEF DESCRIPTION OF THE DRAWINGS

In the drawings:

FIG. 3 is a perspective view of a distal end of a stylet for the needle assembly of FIG. 2.

FIG. 4 is a perspective view of a distal end of a spoon cannula for the needle assembly of FIG. 2.

FIG. 5 is a top view of a distal end of the spoon cannula of FIG. 4.

FIG. 29 is a perspective view of a distal end of an alternative embodiment of a spoon cannula for the needle assembly of FIG. 2.

FIG. 30 is a top view of a distal end of the spoon cannula of FIG. 29.

FIG. 31 a cross-sectional view of a distal end of the needle assembly with the spoon cannula of FIG. 29, with the needle assembly shown in a fired position.

FIG. 33 is a perspective view of a distal end of an embodiment of a spoon cannula for the needle assembly of FIG. 32.

FIG. 34 is a top perspective view of a distal end of an inner coring cannula for the needle assembly of FIG. 32.

FIG. 35 is a top view of a distal end of the inner coring cannula of FIG. 34.

Figure 1:
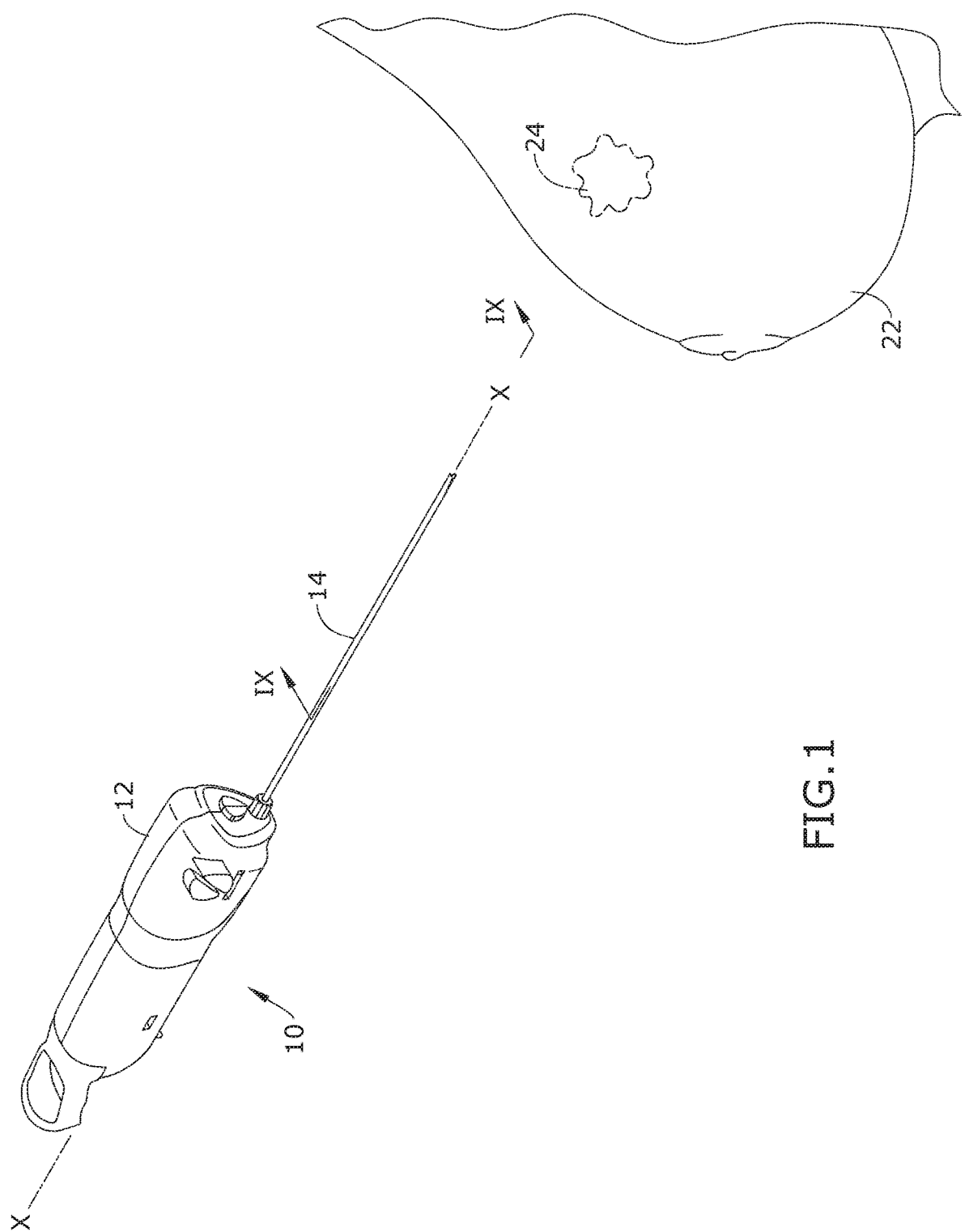
FIG. 1 is a perspective view of a lesion within a tissue mass and a full core biopsy device according one embodiment of the invention.
Figure 2:
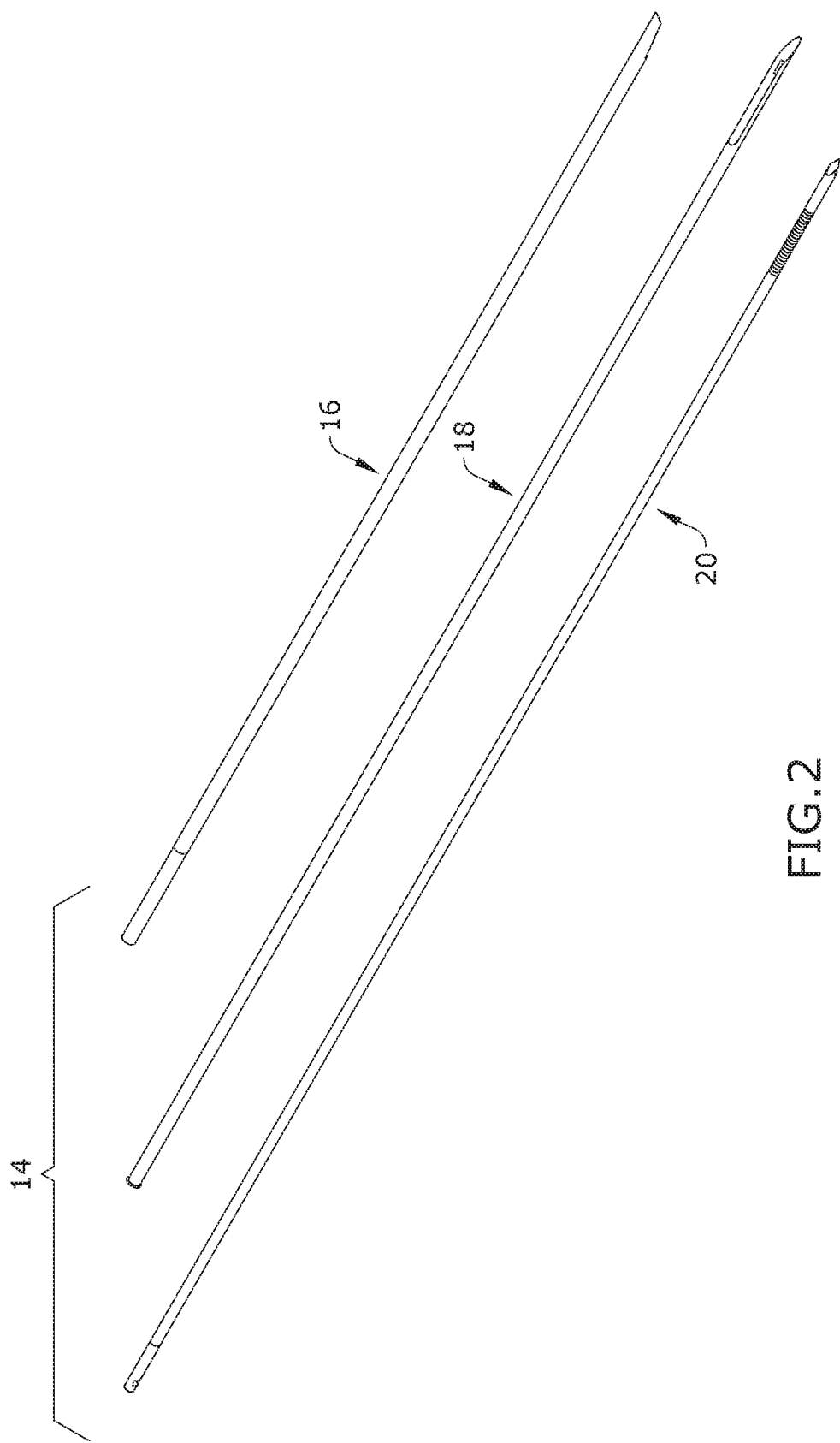
FIG. 2 is an exploded view of a needle assembly of the full core biopsy device from FIG. 1.

The figures referred to above are not necessarily drawn to scale, should be understood to provide a representation of particular embodiments of the disclosure, and are merely conceptual in nature and illustrative of the principles involved. Some features depicted in the drawings may have been enlarged or distorted relative to others to facilitate explanation and understanding.

DETAILED DESCRIPTION

The invention relates to biopsy devices for obtaining biopsy samples from tissue. In one of its aspects, the invention relates to a full core biopsy device for obtaining biopsy samples from tissue, and more particularly, to a full core biopsy device having an excising finger for separating the core biopsy sample from the tissue. In another aspect, the invention relates to a method of operating a full core biopsy device having an excising finger for separating the core biopsy sample from the tissue. In yet another aspect, the invention relates to a method of obtaining a full core tissue sample from a tissue mass.

FIG. 1 is a perspective view of a full core biopsy device 10 according one embodiment of the invention. The full core biopsy device 10 can include an actuator assembly 12 structurally and operably connected to a needle assembly 14. The needle assembly 14 can be utilized to penetrate a tissue mass 22 for obtaining a core biopsy sample, alternately referred to as a biopsy specimen, from a target area in the tissue mass 22, such as a lesion 24, as more specifically described hereinafter.

An embodiment of the actuator assembly 12 is described and illustrated herein comprising an automated, integrated hand-held device capable of controlling the acquisition and removal of a tissue specimen or a core biopsy sample from the lesion 24. An actuator assembly 12 is preferably utilized that is capable of at least semi-automatic firing of the needle assembly 14, with the additional capability of firing a pair of telescoping cannulas with one triggering action, or firing an inner cannula and an outer cannula independently. As described and illustrated herein, in one embodiment the actuator assembly 12 is capable of controlled translational or axial advancement of an outer cannula over an inner cannula after the inner cannula has been fired to excise the core biopsy sample from the surrounding lesion 24.

The biopsy device 10 has an axis X defined by the needle assembly 14 and extending through the actuator assembly 12 as shown in FIG. 1. The axis X also defines an insertion axis of the needle assembly 14 into the tissue mass 22. As used herein, the axis X also defines a longitudinal axis of each member of the needle assembly 14. The axis X can also illustrate a centerline of one or more elements of the needle assembly 14. The members of the needle assembly 14 are coaxially and/or concentrically arranged on the axis X. For the embodiment shown herein, the needle assembly 14 can project from a distal end of the actuator assembly 12 and can be disposed closer to a lower end of the actuator assembly 12 than an upper end and substantially at the center of the actuator assembly 12. However, while the axis X is illustrated extending along the center of the actuator assembly 12, in alternate embodiments it may be off-center depending on the configuration of the actuator assembly 12 for the needle assembly 14.

Referring now to FIGS. 2-9, the needle assembly 14 comprises an outer coring cannula 16, an inner spoon cannula 18, and a stylet 20 in coaxially telescoping relationship. As used herein with respect to the coring cannula 16, the spoon cannula 18, and the stylet 20, the terms "distal" and "forward" refer to or in a direction toward that end of the cannulas 16, 18 and/or the stylet 20 that is directed toward the lesion 24 and away from the actuator assembly 12. "Proximal" or "rearward" thus refers to or in a direction toward that end of the cannulas 16, 18 and/or the stylet 20 that is directed away from the lesion 24 and toward the actuator assembly 12. Preferably, the coring cannula 16, the spoon cannula 18, and the stylet 20 are fabricated of a well-known surgically suitable material, such as stainless steel. At least a portion of the coring cannula 16, the spoon cannula 18, and the stylet 20 can be made from material, shaped or provided with markings that enhance the visibility of the elements with an imaging system including, but not limited to radiography, ultrasound, or MRI.

Referring specifically to FIG. 3, the stylet 20 is an elongated, solid cylindrical member comprising a stylet body 30 terminating in a penetration tip 34 at a distal end thereof. The penetration tip 34 can have various tip shapes, including, but not limited to, beveled, diamond, conical, or multi-faceted (as shown herein). The stylet body 30 has a maximum stylet diameter 32 which is sized for slidable and coaxial insertion through the spoon cannula 18. The stylet body 30 can be shaped or provided with markings 36 near the distal end thereof that enhance the visibility of the stylet 20 with a particular imaging system, including radiography, ultrasound, or MRI.

Referring specifically to FIG. 4, the spoon cannula 18 is an elongated, tubular member having an enclosed section 40 smoothly transitioning distally to a spoon 42. The enclosed section 40 comprises an annular wall 44 having an outer diameter 52 defining a lumen 56 having an inner diameter 54. The spoon 42 comprises an arcuate wall 46 contiguous with a portion of the annular wall 44. The maximum outer diameter and the maximum inner diameter of the spoon 42 can be the same as the outer diameter 52 and the inner diameter 54 of the enclosed section 40.

In one embodiment, the arcuate wall 46 is semicircular, defining a central angle of 180°. Alternatively, the arcuate wall 46 can comprise an arc length defining a central angle ranging between about 120° and somewhat greater than 180°. An arc length greater than 180° will provide enhanced support of the biopsy sample and will minimize the risk of unintended sample deformation during removal of the sample from the spoon 42. The inner diameter 54 is greater than the maximum stylet diameter 32 so that the stylet 20 can be slidably received within the lumen 56 and so that the spoon cannula 18 and stylet 20 can move axially relative to each other, i.e. translate along the axis X.

The arcuate wall 46 terminates at a distal end in an insertion tip 48. The distal edge of the arcuate wall 46 at the insertion tip 48 is inclined relative to the axis X define a beveled edge 50. The beveled edge 50 can be provided with a secondary bevel, which in effect sharpens the beveled edge 50, to enhance the penetration capability of the spoon cannula 18 into the tissue mass 22 and the lesion 24. In other embodiments, the insertion tip 48 can have various edge shapes, including, but not limited to, a parabolic beveled edge, an elliptical beveled edge, a serrated edge, a toothed edge or a scalloped edges.

The arcuate wall 46 can further include a pair of spaced-apart longitudinal spoon edges 58 extending proximally from the insertion tip 48, i.e. from the ends of the beveled edge 50, and are joined by a lateral spoon edge 60 spaced proximally of the insertion tip 48. The length of the spoon 42 is generally defined as the distance from the lateral spoon edge 60 to the distal end of the insertion tip 48. The longitudinal spoon edges 58 are elongated in the direction of the axis X, and may be parallel to each other, and may lie substantially parallel to the axis X. The lateral spoon edge 60 may curve around the axis X to join the longitudinal spoon edges 58. It is contemplated that the spaced spoon edges 50, 58, 60 can define a specimen opening that can terminate in the insertion tip 48.

Referring to FIGS. 4-5, the spoon 42 is provided with a slot or open window 62 adjacent the insertion tip 48. The window 62 as shown herein is a generally rectilinear opening in the arcuate wall 46 comprising a pair of parallel, spaced-apart longitudinal window edges 64 defining a window width 66 and joined by a proximal lateral window edge 68 and a distal lateral window edge 70 adjacent the insertion tip 48. The longitudinal window edges 64 may lie substantially parallel to the axis X, and may be longer than lateral window edges 68, 70. The lateral window edges 68, 70 may lie substantially perpendicular to the axis X. Further, the window 62 may be diametrically opposed to an open top of the spoon 42 defined by the longitudinal spoon edges 58.

Figure 6:
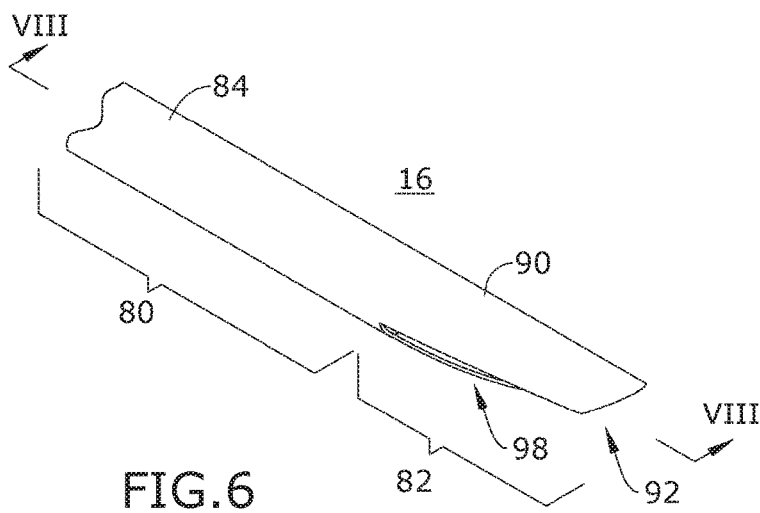
FIG. 6 is a top perspective view of a distal end of a coring cannula for the needle assembly of FIG. 2.
Figure 7:
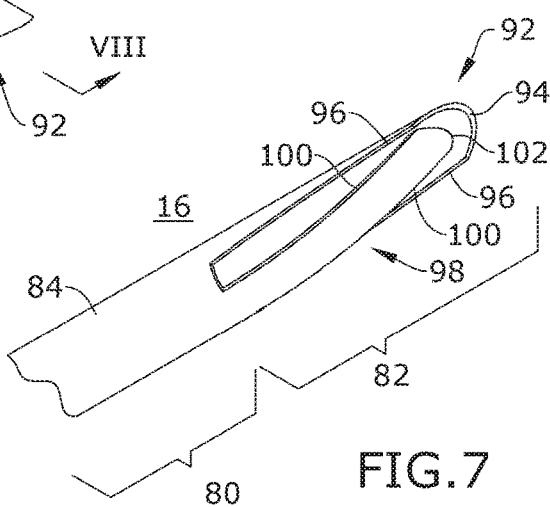
FIG. 7 is a bottom perspective view of a distal end of the coring cannula of FIG. 6.
Figure 8:
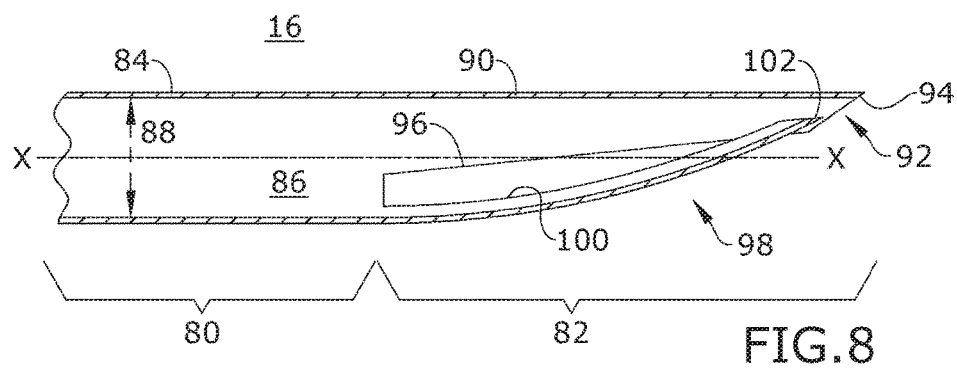
FIG. 8 is a cross-sectional view of a distal end of the coring cannula taken along line VIII-VIII of FIG. 6.
Figure 9:
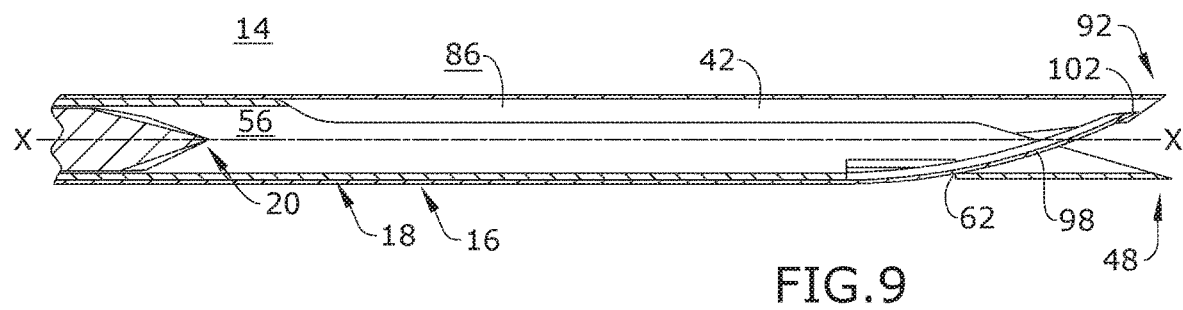
FIG. 9 a cross-sectional view of a distal end of the needle assembly taken along line IX-IX of FIG. 1, with the needle assembly shown in a fired position.

Referring to FIGS. 6-8, the coring cannula 16 is an elongated, tubular member having an enclosed section 80 which transitions distally to a cutting section 82. The enclosed section 80 comprises an annular wall 84 defining a lumen 86 having an inner diameter 88. The inner diameter 88 of the coring cannula 16 is somewhat greater than the outer diameter 52 of the spoon cannula 18 so that the spoon cannula 18 can be slidably received within the lumen 86 of the coring cannula 16 and so that the coring cannula 16 and the spoon cannula 18 can move axially relative to each other, i.e. translate along the axis X.

The cutting section 82 comprises an arcuate wall 90 contiguous with a portion of the annular wall 84. In one embodiment, the arcuate wall 90 is semicircular, defining a central angle of 180°. Alternatively, the arcuate wall 90 can comprise an arc length defining a central angle ranging between about 120° and somewhat greater than 180°.

The arcuate wall 90 terminates at a distal end in a cutting tip 92. The cutting tip 92 is inclined relative to the axis X to define a beveled edge 94. The beveled edge 94 can be provided with a secondary bevel, which in effect sharpens the beveled edge 94, to enhance the penetration capability of the coring cannula 16 into the tissue mass 22 and the lesion 24. In other embodiments, the cutting tip 92 can have various edge shapes, including, but not limited to, a parabolic beveled edge, an elliptical beveled edge, a serrated edge, a toothed edge or a scalloped edges.

The arcuate wall 90 can further include a pair of spaced-apart longitudinal cutting edges 96 extending proximally from the cutting tip 92, i.e. from the ends of the beveled edge 94, and are joined with a distal end of the enclosed section 80. The length of the cutting section 82 is generally defined as the distance from the distal end of enclosed section 80 to the distal end of the cutting tip 92. The longitudinal cutting edges 96 are elongated in the direction of the axis X, and may be parallel to each other, and may lie transversely to the axis X.

The cutting section 82 of the coring cannula 16 also includes an excising finger 98 extending generally longitudinally in the direction of axis X. As shown herein, the excising finger 98 can be diametrically opposed to the arcuate wall 90 defining the cutting tip 92, and may be substantially coextensive with the arcuate wall 90. The excising finger 98 is adapted to have a resilience which enables the excising finger 98 to elastically deflect away from the axis X and to return to an at-rest configuration as best seen in FIG. 8. As used herein with respect to the excising finger 98, the term 'resilience' and variations thereof include an excising finger 98 which may be elastically deformed at least once, such that when a force which deflects the excising finger 98 away from the axis X is removed or no longer applied, the excising finger 98 returns to its original shape by moving back to the at-rest configuration, or substantially to its original shape by moving at least partially back toward the axis X. The excising finger 98 is further yieldable or flexible, in that it is capable of being elastically deflected away from the axis X and of returning to an at-rest configuration without breaking.

The excising finger 98 can be angled or arcuate in the at-rest configuration, such that it extends or curved toward the axis X. The excising finger 98 can further have a generally rectilinear shape comprising pair of spaced-apart longitudinal finger edges 100 extending distally from the distal end of the enclosed section 80 and a distal lateral finger edge 102 which joins the longitudinal finger edges 100. The length of the excising finger 98 is generally defined as the distance from the distal end of the enclosed section 80 to the distal end of the distal finger edge 102. The longitudinal finger edges 100 are elongated in the direction of the axis X, and may be parallel to each other, and may lie generally transverse to the axis X in the at-rest configuration. The distal finger edge 102 may curve around the axis X to join the longitudinal spoon edges 58. Other suitable shapes for the excising finger 98 are possible, including, but are not limited to, a trapezoidal shape where the longitudinal finger edges 100 taper toward the distal finger edge 102.

One or both of the finger edges 100, 102 can be beveled to enhance the penetration and cutting characteristics of the excising finger 98, with or without a secondary bevel. In other embodiments, the distal lateral finger edge 102 can have various edge shapes, including, but not limited to, a parabolic beveled edge, an elliptical beveled edge, a serrated edge, a toothed edge or a scalloped edges FIG. 9 a cross-sectional view of a distal end of the assembled needle assembly 14, taken along line IX-IX of FIG. 1. The needle assembly 14 is assembled by installing the stylet 20 into the lumen 56 of the spoon cannula 18, and installing the spoon cannula 18 into the lumen 86 of the coring cannula 16, to provide a telescoping assembly wherein the coring cannula 16 is slidably and coaxially disposed around the spoon cannula 18, which is slidably and coaxially disposed around the stylet 20.

The excising finger 98 is adapted for slidable insertion through the window 62 in the spoon 42. The excising finger 98 is pre-formed, like a spring, to be biased toward the axis X. As described in further detail below, as the coring cannula 16 is advanced axially over the spoon cannula 18, the finger 98 will resiliently return to its at-rest position as it reaches the window 62. As illustrated, the excising finger 98 is curved inwardly toward the axis X so that the distal edge 102 extends to, and preferably crosses, the axis X. The extension of the excising finger 98 at least to the axis X will enable the excising finger 98 to completely excise a biopsy sample when the finger 98 is extended through the window 62. In this position, the insertion tip 48 and cutting tip 92 of the cannulas may be substantially aligned.

The assembled needle assembly 14 is operably attached to the actuator assembly 12 (FIG. 1). The actuator assembly 12 (FIG. 1) can be of any suitable construction as long as it can axially extend or translate at least the coring and spoon cannulas 16, 18 in a controlled manner to ultimately place the coring cannula 16 in the excising position shown in FIG. 9, and ensure the separation of the biopsy sample from the tissue mass 22 upon withdrawal of the needle assembly 14 from the tissue mass 22.

FIGS. 10-21 illustrate a one embodiment of an actuator assembly 12 for axially extending or translating the coring and spoon cannulas 16, 18 in a controlled manner. As used herein, the term "distal" or "forward" refers to or in a direction toward that end of the actuator assembly 12 and its component parts that is directed toward the needle assembly 14. "Proximal" or "rearward" thus refers to or in a direction toward that end of the actuator assembly 12 and its component parts that is directed away from the needle assembly 14.

The actuator assembly 12 comprises a hand-held device capable of controlling the acquisition and removal of the biopsy sample, from the lesion 24 through the arming and firing of the needle assembly 14. As illustrated, the cocking is manual and the firing is automatic or semi-automatic. The actuator assembly 12 of the present embodiment is capable of arming the cannulas 16, 18 independently. The actuator assembly 12 has the additional capability of firing the cannulas 16, 18 with one triggering action, or firing the cannulas 16, 18 independently. Re-arming of the biopsy device 10 after firing exposes the biopsy sample, and allows easy retrieval of the biopsy sample from the needle assembly 14. The actuator assembly 12 also functions as a handle for holding the biopsy device 10.

Figure 10:
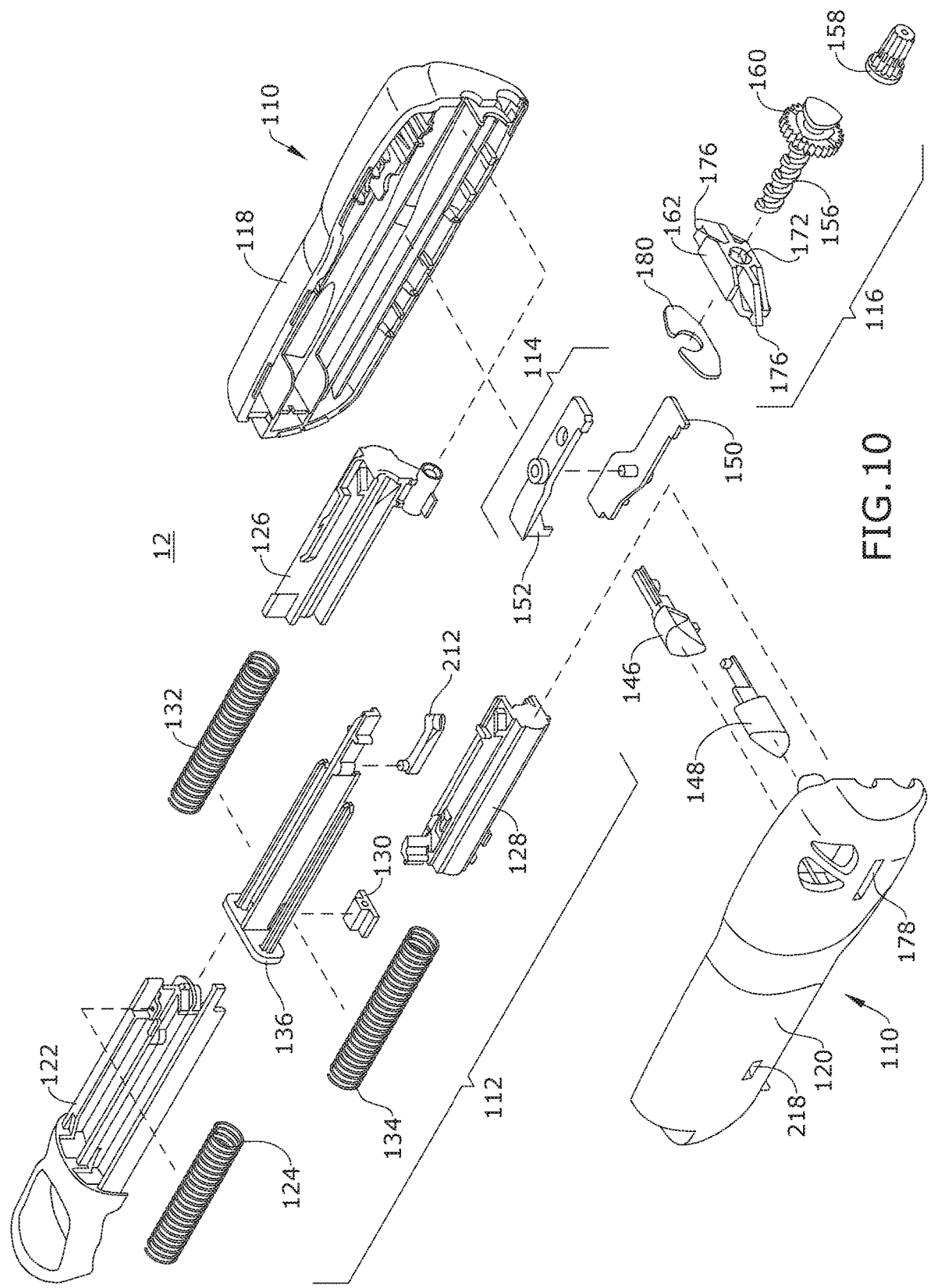
FIG. 10 is an exploded view of an actuator assembly of the full core biopsy device from FIG. 1.
Figure 11:
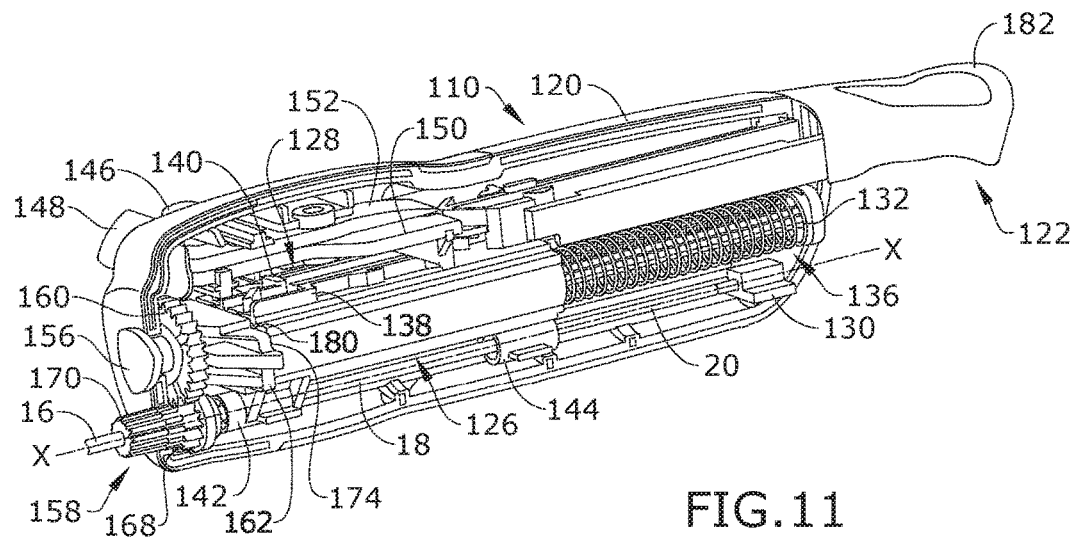
FIG. 11 is a perspective view of the full core biopsy device shown in an unarmed or fired position, with a portion of an outer housing removed to show internal components of the device.
Figure 12:
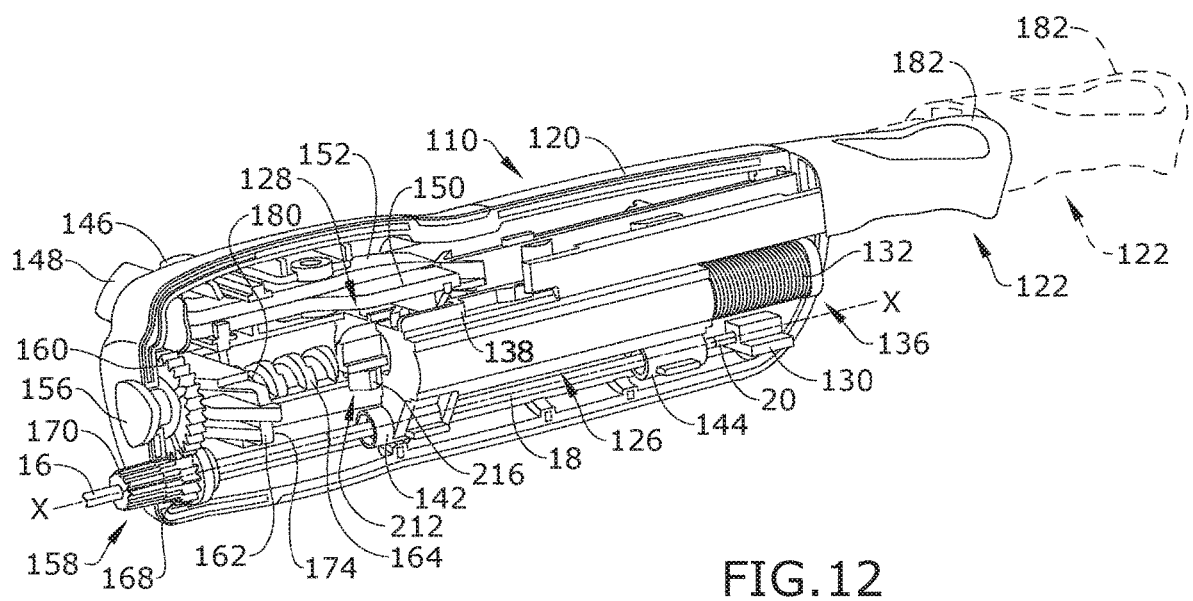
FIG. 12 is a perspective view similar to FIG. 11, with the full core biopsy device shown in an armed position.

Referring to FIGS. 10-12, the actuator assembly 12 comprises an outer housing 110 that supports the needle assembly 14 and both the internal and external components of the actuator assembly 12, including an arming/firing assembly 112, a trigger assembly 114 and a sample size control assembly 116. The outer housing 110 can, for example include a first housing shell 118 and a second housing shell 120 adapted for cooperative registry. The housing shells 118, 120 are contoured and configured with openings, bosses, rails, and the like, for operational support of the elements comprising the core biopsy device 10, including the components of the arming/firing assembly 112, a trigger assembly 114 and a sample size control assembly 116, and well as the needle assembly 14.

The arming/firing assembly 112 is configured to arm the core biopsy device 10, i.e. ready the needle assembly 14 for firing, as well as to fire the needle assembly 14 when triggered. In the present embodiment, the arming/firing assembly 112 includes an arming element 122, an arming element spring 124, a coring cannula carriage 126 which carries the coring cannula 16, a spoon cannula carriage 128 which carries the spoon cannula 18, a stylet holder 130 which carries the stylet 20, a coring cannula spring 132, a spoon cannula spring 134, a spring guide 136.

The arming element 122 is slidably mounted to the outer housing 110 for movement between a first, retracted position (FIG. 11) and a second, extended position (shown in phantom in FIG. 12), which defines a single arming stroke of the core biopsy device 10. As illustrated herein, in the first position, the arming element 122 is retracted into the outer housing 110 by the spring 124 and in the second position; the arming element 122 is extended in a proximal direction from the outer housing 110.

Figure 13:
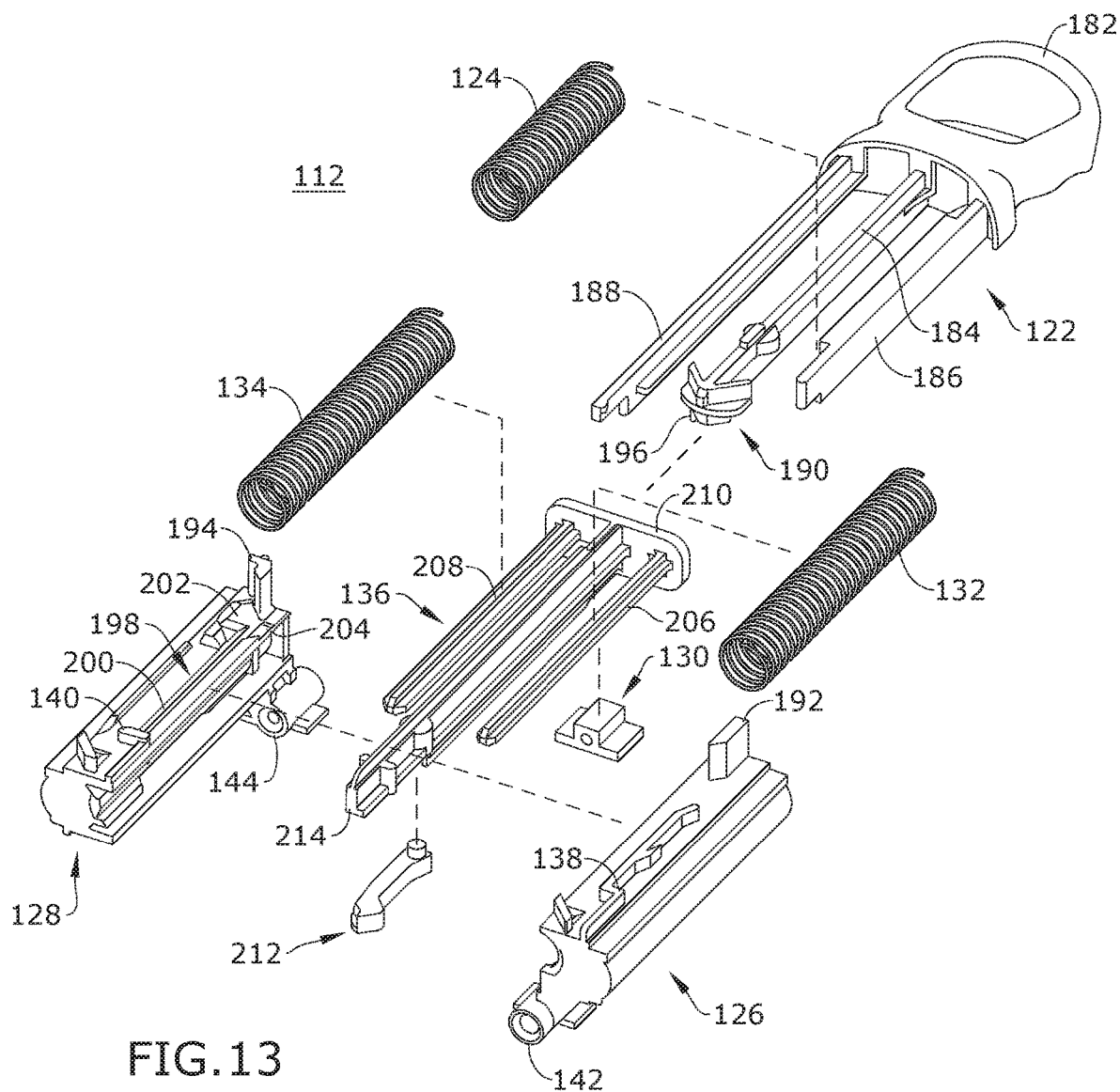
FIG. 13 is an exploded view of an arming/firing assembly of the actuator assembly of the full core biopsy device from FIG. 1.

Referring additionally to FIG. 13, the arming element 122 can include a pull 182 having an arming member 184 extending distally from the pull 182 between two distally extending, laterally spaced alignment members 186, 188. The pull 182 is provided on the exterior of the outer housing 110, with the members 184, 186, 188 extending into the housing 110 to guide the movement of the arming element 122 relative to the outer housing 110. The pull 182 is configured to be grasped by the user to draw the arming element 122 to the extended position in a proximal direction. As such, the pull 182 can be contoured to provide a comfortable grip to the user; as illustrated herein, the pull 182 is ring-shaped and includes two contoured portions against which the user can brace a finger or thumb. The cocking element spring 124 is attached between one of the alignment members 186 and the outer housing 110, and functions to bias the arming element 122 to the retracted position.

The arming member 184 is flexible or resilient elongated member, and can extend substantially along the axis X. A distal free end of the arming member 184 opposite the pull 182 includes a catch 190. The arming member 184 can be configured to be flexible or resilient such that the catch 190 can be displaced or deflected laterally from the axis X. As illustrated herein, the catch 190 comprises an arrow-shaped lug formed by two angled arms.

The cannula carriages 126, 128 are sequentially engaged by the arming element 122 to draw the carriages 126, 128, and therefore the coring cannula 16 and the spoon cannula 18, back to an armed position (FIG. 12). The cannula carriages 126, 128 are restrained by the outer housing 110 for axial or translation movement within the outer housing 110 along the axis X. The cannula carriages 126, 128 each have a respective retaining member or catch 138, 140 that releasably locks the carriages 126, 128 in the armed position relative to the outer housing 110. At least a portion of the catches 138, 140 may be transverse to the axis X. The cannula carriages 126, 128 further each have a respective cannula holder 142, 144 which receives a proximal end of the coring cannula 16 and the spoon cannula 18, respectively, to mount or affix the coring cannula 16 and the spoon cannula 18 on the carriages 126, 128.

The cannula holders 142, 144 are aligned with each other and can define the needle axis X along which the cannulas 16, 18 lie, and as shown herein, the coring cannula holder 142 can be disposed distally of the spoon cannula holder 144 so that the spoon cannula carriage 128 can be fired before the coring cannula carriage 128. While the cannula holders 142, 144 are aligned, the coring cannula carriage 126 can generally be laterally offset from the axis X in a first lateral direction toward the first housing shell 118, and the spoon cannula carriage 128 can be laterally offset from the axis X in the second lateral direction toward the second housing shell 120. The stylet holder 130 is also aligned with the cannula holders 142, 144 for coaxial arrangement of the stylet 20 with the cannulas 16, 18. The stylet holder 130 is further fixed with or otherwise stationarily mounted within the outer housing 110, and does not slide or move when arming or firing the core biopsy device 10.

The coring cannula carriage 126 further comprises a strike 192 in the form of a lug having an angled distal face projecting from an upper surface of the carriage 126 that is adapted to be engaged by the catch 190 on the arming element 122. Both the coring cannula catch 138 and the cannula holder 142 are positioned distally of the strike 192 on the carriage 126. The strike 192 is laterally offset from the cannula holder 142, and is therefore laterally offset from the axis X.

The spoon cannula carriage 128 further comprises a strike 194 in the form of a lug having an angled distal face projecting from an upper surface of the carriage 128 that is adapted to be engaged by the catch 190 on the arming element 122. The spoon cannula catch 140 is positioned distally of the strike 194 on the carriage 126, and the cannula holder 144 positioned substantially beneath the strike 194. The strike 194 is laterally offset from the cannula holder 144, and is therefore laterally offset from the axis X.

When assembled with the carriages 126, 128 in the fired position, the angled distal face on the coring cannula strike 192 is distally spaced from the angled distal face on the spoon cannula strike 194. The strikes 192, 194 are further laterally offset from the axis X in opposing directions.

The biopsy device 10 can further include an alignment assembly that is configured to maintain the arming member 184 of the arming element 122 in alignment with the axis X.

The alignment assembly as shown herein includes a guide pin 196 that extends downwardly from the catch 190 of the arming member 184, and a track 198 for guiding the movement of the catch 190 during the arming strokes. As illustrated herein, the track 198 is formed as an elongated recess in an upper surface of the spoon cannula carriage 128. The guide pin 196 rides along the track 198 during an arming stroke of the arming element 122 to ensure that the arming member 184 travels along the axis X.

The track 198 can include a linear section 200 that is parallel to the axis X and an angled section 202 that is continuous with the linear section 200 and that is oriented at an angle with respect to the axis X. The angled section 202 is configured to guide the catch 190 towards the spoon cannula strike 194. The track 198 can further include an exit ramp 204 formed in the linear section 200. The exit ramp 204 is medial of, and just distal to, the angled section 202. The exit ramp 204 permits the guide pin 196 to leave the track 198 when the catch 190 engages the coring cannula strike 192 during a first arming stroke, and thus not follow the track 198 to the angled section 202, which permits the coring cannula carriage 126 to be armed first.

The spring guide 136 mounts the cannula springs 132, 134, which act to bias the cannula carriages 126, 128 toward the fired position (FIG. 11). The spring guide 136 is fixed with or otherwise stationarily mounted within the outer housing 110 and includes two laterally spaced rods 206, 208 that extend orthogonally from a base 210. The carriages 126, 128 can be at least partially hollow to form spring cavities (not shown) which at least partially receive the rods 206, 208 and springs 132, 134. When assembled, the rods 206, 208 extend into spring cavities on the cannula carriages 126, 128, respectively, with the coring cannula spring 132 received about the rod 206 and the spoon cannula spring 134 received about the rod 208.

A delay arm 212 can be provided to delay movement of the coring cannula carriage 126 during firing. As shown herein, the delay arm 212 is movably mounted on the spring guide 136, and can, for example, be pivotally mounted to an elongated member 214 that extends from the base 210 in between the rods 206, 208. As best seen in FIG. 12, the delay arm 212 has a distal projection 216 which is adapted to project at least partially in front of the distal face of the coring cannula carriage 126 when in the armed position.

The trigger assembly 114 is configured to trigger the needle assembly 14 to fire, i.e. release the needle assembly 14 from the armed position. In the present embodiment, the trigger assembly 114 can include a first button 146, a second button 148, a coring cannula retainer 150, and a spoon cannula retainer 152. The first button 146 functions to fire the spoon cannula 18 alone for a semi-automatic firing of the core biopsy device 10. The second button 148 functions to sequentially fire the spoon cannula 18 and the coring cannula 16 in rapid succession for an automatic operation of the core biopsy device 10, or, if the spoon cannula 18 has already been fired via the first button 146, to fire the coring cannula 16 alone to complete the semi-automatic firing.

The coring cannula retainer 150 is operably coupled between the second button 148 and the coring cannula carriage 126. The coring cannula retainer 150 engages the catch 138 formed on the coring cannula carriage 126 to releasably retain the coring cannula carriage 126 in the armed position. The coring cannula retainer 150 is configured to be moved into engagement with the catch 138 during the first arming stroke of the core biopsy device 10.

The spoon cannula retainer 152 is operably coupled between the first button 146 and the spoon cannula carriage 128. The spoon cannula retainer 152 engages the catch 140 formed on the spoon cannula carriage 128 to releasably retain the spoon cannula carriage 128 in the armed position. The spoon cannula retainer 152 is configured to be moved into engagement with the catch 140 during the second arming stroke of the biopsy device 10.

Referring to FIGS. 10-12, the sample size control assembly 116 is configured to enable the user to select the biopsy sample size to be collected, i.e. setting the throw or throw distance of the needle assembly 14. In the present embodiment, the sample size control assembly 116 can include an adjuster member 156, actuator 158, an adjuster gear 160 coupling the adjuster member 156 and the actuator 158, and a throw stop 162 coupled to the adjuster member 156. The throw stop 162 is linearly movable along adjuster member 156. The location of the throw stop 162 relative to the outer housing 110 will determine the distance the carriages 126, 128 can travel, and consequently can determine the fired position of the carriages 126, 128.

The adjuster member 156 has an elongated, somewhat screw-shaped threaded body 164 which rotatably mounts the adjuster member 156 on the outer housing 110. The adjuster gear 160 is keyed to or otherwise fixed on the adjuster member 156 for rotation therewith.

The actuator 158 comprises an annular body having a wheel gear 168 and a nose portion or wheel 170, and defines an open channel through which the needle assembly 14 extends. The wheel gear 168 is enmeshed with the adjuster gear 160 to operably couple the actuator 158 with the adjuster member 156. The actuator 158 is rotatably mounted on the outer housing 110, with the wheel 170 projecting at least partially from the distal end of the outer housing 110 for use in operating the sample size control assembly 116.

The throw stop 162 comprises a movable body defining an open ended threaded channelway 172 which receives the threaded body 164 of the adjuster member 156. A proximal face of the throw stop 162 serves as a stop surface 174 which the cannula carriages 126, 128 will strike when the core biopsy device 10 is fired. Therefore, the location of the throw stop 162 relative to the outer housing 110 will determine the distance the cannula 1 carriages 126, 128 can travel relative to the outer housing 110.

The throw stop 162 can further include at least one indicator 176, shown herein in the form of opposing tips on the movable body, which is visible through at least one window 178 in the outer housing 110. The at least one indicator 176 can indicate the position of the throw stop 162 relative to the outer housing 110, which in turn can indicate either the throw distance the core biopsy device 10 is set to or the specimen size the core biopsy device 10 is set to collect, since the position of the throw stop 162 determines the distance the cannula carriages 126, 128 can travel relative to the outer housing 110. Indicia can be provided as makings on the outer housing 110 adjacent the at least one window 178 to indicate various throw distances or specimen sizes that can be collected by the core biopsy device 10, with the at least one indicator 176 of the throw stop 162 indicating the throw distance or specimen length that the core biopsy device 10 is set to take.

A damper 180 can optionally be provided between the throw stop 162 and the carriages 126, 128 to provide noise dampening, vibration dampening, and/or shock absorption. As illustrated herein, the damper 180 comprises a relatively flat member located on the stop surface 174 of the throw stop 162, in which case the cannula carriages 126, 128 will strike the damper 180 when fired. The damper 180 can be attached to the throw stop 162 using a pressure sensitive adhesive.

The damper 180 can be fabricated from a material that provides noise dampening, vibration dampening, and/or shock absorption when contacted by the cannula carriages 126, 128, such as a polyurethane foam. The damper 180 can be configured to dampen the noise associated with firing the core biopsy device 10. Optionally, the damper 180 can limit the noise to a level below that which triggers the acoustic startle reflex (also known as the acoustic startle response, both abbreviated as "ASR"), which is a reflex pattern or response a sudden unexpected stimulus, such as a loud noise, in the average human or in the majority of humans. Optionally, the damper 180 can limit the noise to under 115 decibels.

Figure 14:
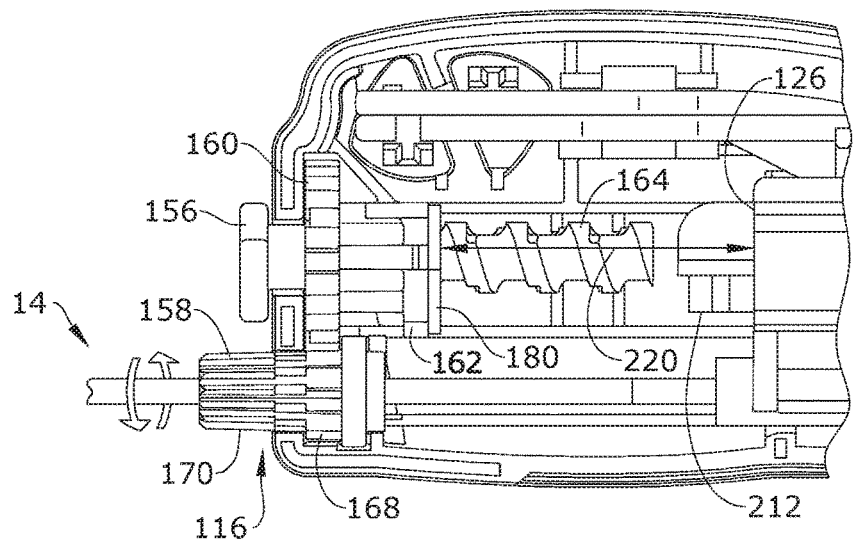
FIG. 14 is a side view of a sample size control assembly of the full core biopsy device, illustrating the section of a biopsy sample size to be collected.
Figure 15:
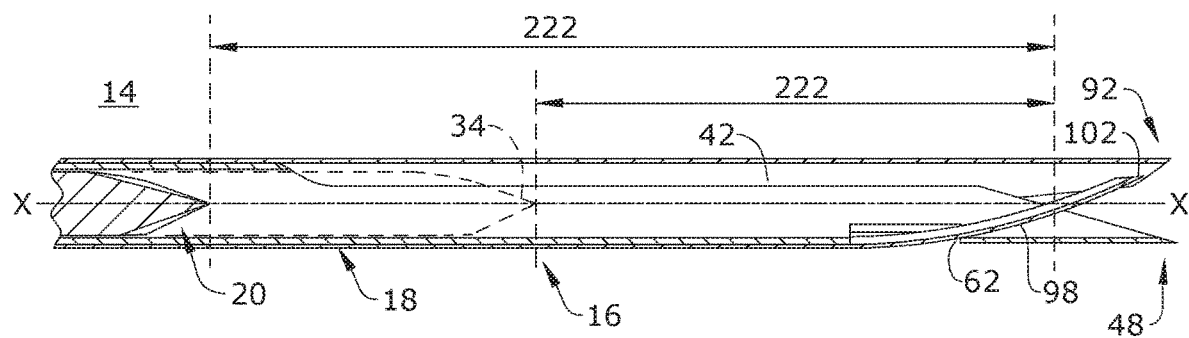
FIG. 15 is a view illustrating the variation of a fired position of the needle assembly upon the section of a biopsy sample size to be collected using the sample size control assembly of FIG. 17.

Referring to FIGS. 14-15, to select or set the sample size, the actuator 158 is rotated using the wheel 170. Rotation is transmitted to the adjuster member 156 by the enmeshed gears 160, 168. The rotation of the adjuster member 156 is in turn translated to linear movement of the throw stop 162 along the threaded body 164. The throw stop 162 will move distally or proximally depending on the direction in which the actuator 158 is rotated, along with the optional damper 180. Since the sample size control assembly 116 relies upon translating rotational motion to linear motion, the throw or sample size can be infinitely adjusted within a minimum and maximum size. Optionally, the throw or sample size can be infinitely adjusted between 15 and 25 mm.

The location of the throw stop 162 or optional damper 180 relative to the outer housing 110 determines the distance the carriages 126, 128 travel, and consequently determines the fired positions of the carriages 126, 128, as well as the distance the cannulas 16, 18 will travel into the lesion 24. Thus, the sample size control assembly 116 can also be characterized as adjusting the throw of the core biopsy device 10. The distance 220 between the throw stop 162 or optional damper 180 and the distal end of the carriages 126, 128 is proportional to the length of the biopsy sample the core biopsy device 10 will collect when fired.

The throw of the biopsy device 10 determines the distance the cannulas 16, 18 extend past the penetration tip 34 of the stylet 20 when fired. Throughout the range of biopsy sizes or throw settings, the cannulas 16, 18 will always extend past the stylet 20 when fired to obtain a biopsy sample. The length 222 of a collected biopsy sample is generally equal to the distance between the penetration tip 34 and the point where the excising finger 98 of the coring cannula 16 crosses the axis X when fired. Therefore, a longer throw or greater distance 220 will produce a specimen having a greater length 222.

One embodiment of the operation of the core biopsy device 10 generally comprises the steps of: (I) arming the core biopsy device 10; (II) selecting the biopsy sample size to be collected, i.e. setting the throw; (III) firing the core biopsy device 10 to collect a biopsy sample; and (IV) collecting the biopsy sample from the core biopsy device 10. It will be apparent to one of ordinary skill that the embodiment of the operation described subsequently can proceed in any logical order and is not limited to the listed sequence. An exemplary description of the operation of the core biopsy device 10 will now be described with reference to FIGS. 16-28 in the context of performing a breast biopsy. However, the core biopsy device 10 is not so limited, and can be utilized to obtain a core biopsy sample from other soft tissues, for example the liver, kidney, or skeletal muscles. FIGS. 16-21 illustrate the various relative positions of the elements of the actuator assembly 12 during operation; these figures, elements of the core biopsy device 10 particularly the outer housing 110, may be either removed or illustrated in phantom to facilitate a complete understanding of the operation of the core biopsy device 10. FIGS. 22-28 illustrate the various relative positions of the elements of the needle assembly 14 during operation.

At the beginning to operation, the core biopsy device 10 is initially in the unarmed or fired position as shown in FIG. 11, and is typically armed prior to introducing the needle assembly 14 into a tissue mass. In the unarmed or fired position, the arming element 122 is urged distally to the retracted position by influence of the spring 124 (FIG. 10), and the carriages 126, 128 are urged distally against the throw stop 162 (or optional damper 180) by their respective springs 132, 134. Optionally, the core biopsy device 10 can be shipped in the unarmed or fired position, and may be a disposable medical device intended for use in obtaining one or more biopsy samples from one tissue mass 22.

Figure 22:
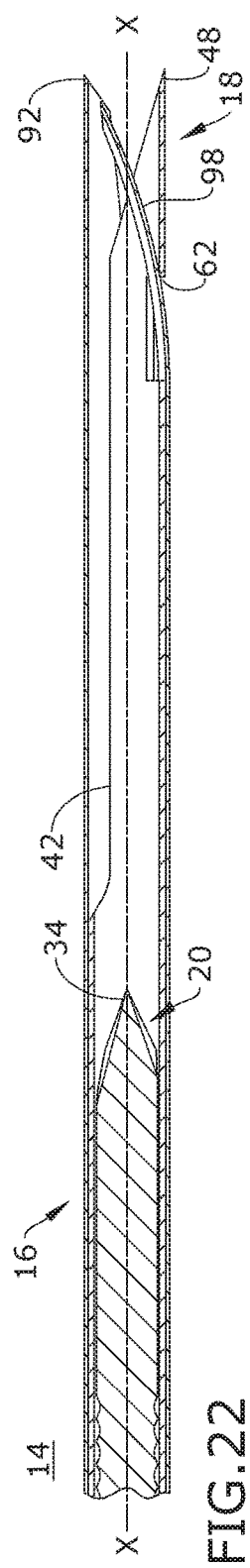
FIGS. 22-28 are longitudinal sectional views of the needle assembly at various steps in the process of obtaining a core biopsy sample.

With reference to FIG. 22, when the core biopsy device 10 is initially in the unarmed or fired position, the needle assembly 14 is in an unarmed or fired configuration. In this configuration, the tips 48, 92 of the cannulas 16, 18 are distal of the penetration tip 34 of the stylet 20. The excising finger 98 of the coring cannula 16 is inserted through the window 62 in the spoon 42 of the spoon cannula 18 and in its at-rest position extending to or crossing the axis X.

Figure 16:
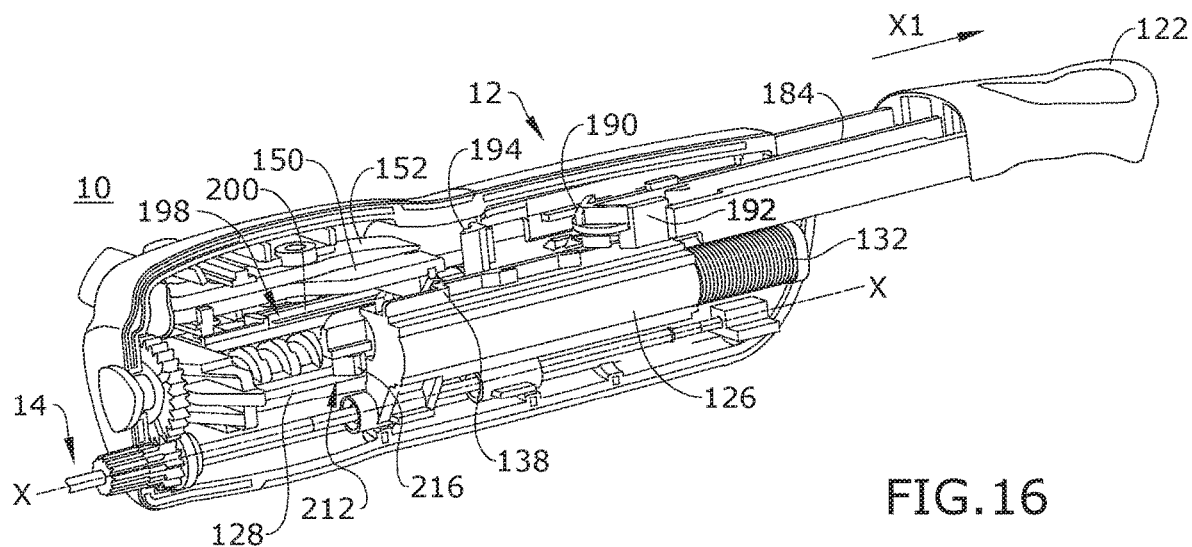
FIG. 16 is a perspective view of the full core biopsy device shown during a first arming stroke, with a portion of an outer housing removed to show internal components of the device.
Figure 17:
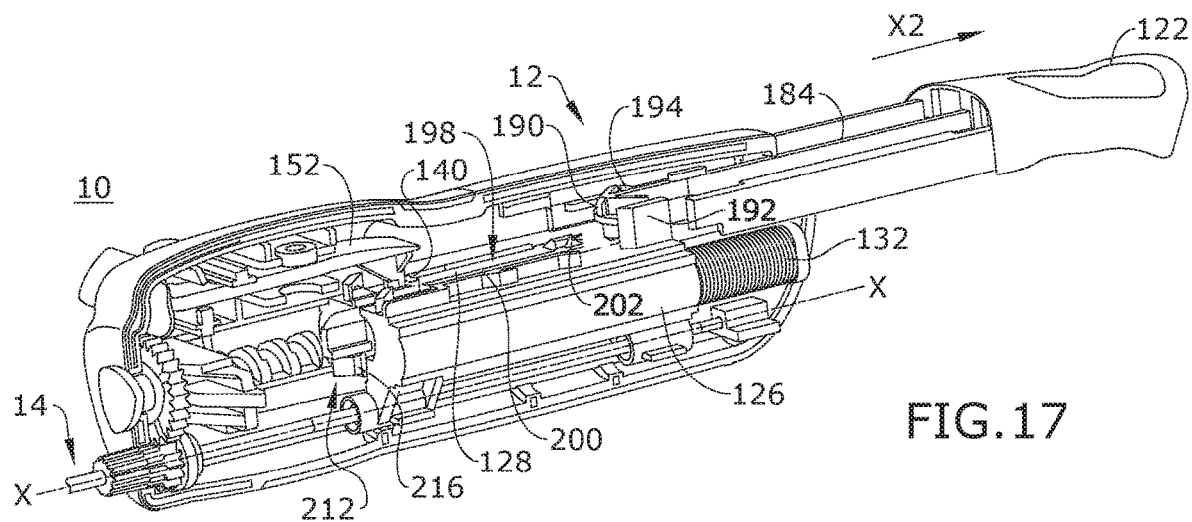
FIG. 17 is a view similar to FIG. 17, with the full core biopsy device shown during a second arming stroke.

Referring to FIGS. 16-17, to arm the core biopsy device 10, the arming element 122 is pulled rearwardly or proximally twice to sequentially retract the coring cannula carriage 126 and the spoon cannula carriage 128 to the armed position, with the retaining catches 138, 140 engaging the retainers 150, 152 to releasably retain the carriages 126, 128 in the armed position.

When the arming element 122 is pulled rearwardly or proximally a first time, as shown in FIG. 16, the guide pin 196 (FIG. 13) on the catch 190 rides along the linear section 200 of the track 198, and the catch 190 will meet the coring cannula strike 192, and the engagement of the angled surfaces thereof deflects the arming member 184 laterally from the axis X. This substantially coincides with the guide pin 196 reaching the end of the linear section 200, and the deflection of the arming member 184 causes the guide pin 196 to ride up the exit ramp 204 and out of the track 198. The catch 190 thus clears the spoon cannula strike 194 during the first arming stroke.

Under continued rearward pulling of arming element 122, the coring cannula carriage 126 is pulled rearwardly relative to the coring cannula retainer 150 to a position where the coring cannula retainer 150 engages the catch 138 formed on the coring cannula carriage 126, thereby retaining or releasably locking the coring cannula carriage 126, and consequently the coring cannula 16, in the armed position.

Figure 23:
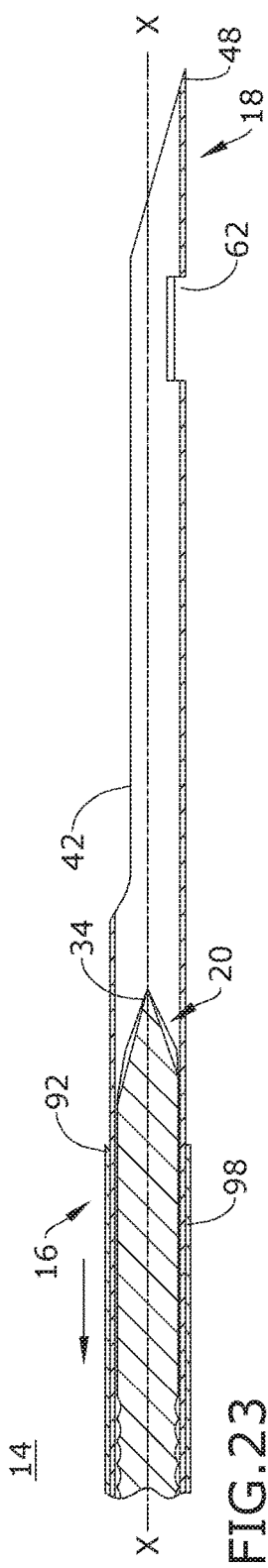

As illustrated in FIG. 23, when the needle assembly 14 is in the partially armed configuration after the first arming stroke, the coring cannula 16 is drawn rearwardly or proximally, and the excising finger 98 is withdrawn from the window 62 and deflected away from the axis X by the spoon cannula 18 and the spoon 42 is exposed. The penetration tip 34 of the stylet 20 extends somewhat distally of the tip 92 of the coring cannula 16.

After the first arming stroke, the arming element 122 returns to the retracted position from the extended position under the influence of the spring 124 or by a controlled release or easing of force on the arming element 122 by the user. As the catch 190 leaves the coring cannula strike 192, the arming member 184 moves back into alignment with the axis X. When the arming element 122 begins to pass over the spoon cannula carriage 128, the catch 190 will meet the spoon cannula strike 194 and the arming member 184 is temporarily deflected until the catch 190 clears the spoon cannula strike 194. The guide pin 196 then reenters the track 198 and slides distally along the linear section 200 until the arming element 122 reaches the retracted position.

When the arming element 122 is pulled rearwardly or proximally a second time, as shown in FIG. 17, the guide pin 196 (FIG. 13) on the catch 190 slides proximally along the linear section 200 of the track 198, and the catch 190 will meet the spoon cannula strike 194, and the engagement of the angled surfaces thereof deflects the arming member 184 laterally from the axis X. This coincides with the guide pin 196 reaching the end of the linear section 200 and entering the angled section 202.

Under continued rearward pulling of arming element 122, the spoon cannula carriage 128 is pulled rearwardly relative to the spoon cannula retainer 152 to a position where spoon cannula retainer 152 engages the catch 140 formed on the spoon cannula carriage 128, thereby retaining or releasably locking the spoon cannula carriage 128, and consequently the spoon cannula 18, in the armed position. It is noted that n FIG. 18, the coring cannula retainer 150 is removed for clarity.

Figure 24:
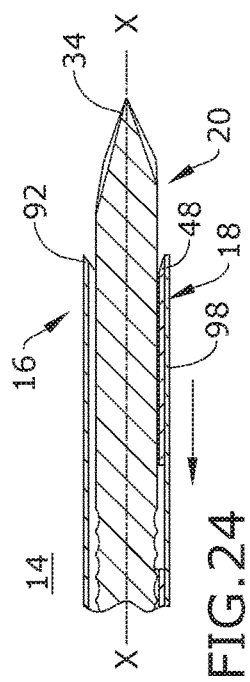

As illustrated in FIG. 24, when the needle assembly 14 is in the fully armed configuration after the second arming stroke, the spoon cannula 18 is drawn rearwardly or proximally, and the penetration tip 34 of the stylet 20 extends somewhat distally of the insertion tip 48 of the spoon cannula 18.

At this point, the core biopsy device 10 is fully armed. After the second arming stroke, the arming element 122 returns to the retracted position from the extended position under the influence of the spring 124 or by a controlled release or easing of force on the pull 182 by the user. When fully armed, a portion of the spoon cannula carriage 126 may be visible through an indicator window 218 (FIG. 10) of the outer housing 110 to indicate to the user that the core biopsy device 10 is fully armed.

After the core biopsy device 10 is fully armed, the biopsy sample size to be collected can optionally be selected using the sample size control assembly 116 as described above with reference to FIG. 14-15. Alternately, the biopsy sample size to be collected can be selected at any time prior to the insertion of the needle assembly 14 into the tissue mass 22. The biopsy sample size may be selected after insertion, but this is not currently preferred.

Figure 25:
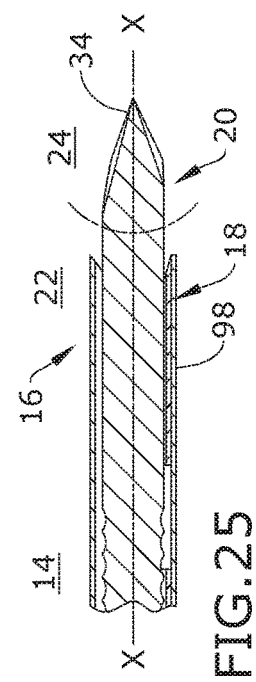

As illustrated in FIG. 25, with the core biopsy device 10 in the fully armed position and the biopsy sample size optionally set as desired, the needle assembly 14 is inserted into the tissue mass 22 so that the penetration tip 34 of the stylet 20 is adjacent to or within the target area or lesion 24. The penetration tip 34 of the stylet 20 can extend somewhat distally of the tips 48, 92 of the cannulas 16, 18 to form a generally solid penetrating tip that facilitates the insertion of the needle assembly 14 into the tissue mass 22. The needle assembly 14 can optionally be guided during insertion using an imaging system. Any suitable imaging system can be used, for example radiography, ultrasound, or MRI. The core biopsy device 10 is then fired for excision of a biopsy sample using the actuator assembly 12.

The actuator assembly 12 can optionally be operated in one of two ways to obtain a biopsy sample, referred to herein as automatic firing or semi-automatic firing. Both the automatic and semi-automatic firing initially fire the spoon cannula 18 into the lesion 24 by releasing the spoon cannula carriage 128 and thereafter fire the coring cannula 16 over the spoon cannula 18 by releasing the coring cannula carriage 126. Also in both the automatic and semi-automatic firing, the stylet 20 remains stationary and does not move. The two firing procedures are illustrated in FIGS. 18-21, in which the outer housing 110 is shown in phantom line to more clearly show the firing procedures.

Figure 18:
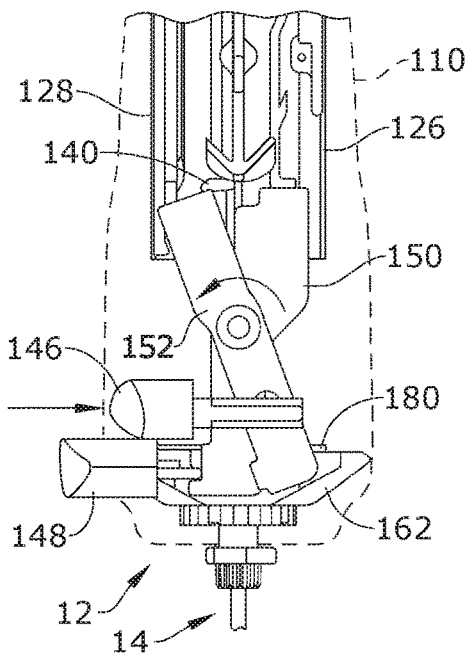
FIGS. 18-21 are top views of the full core biopsy device shown during firing, where the outer housing is shown in phantom line for clarity.
Figure 19:
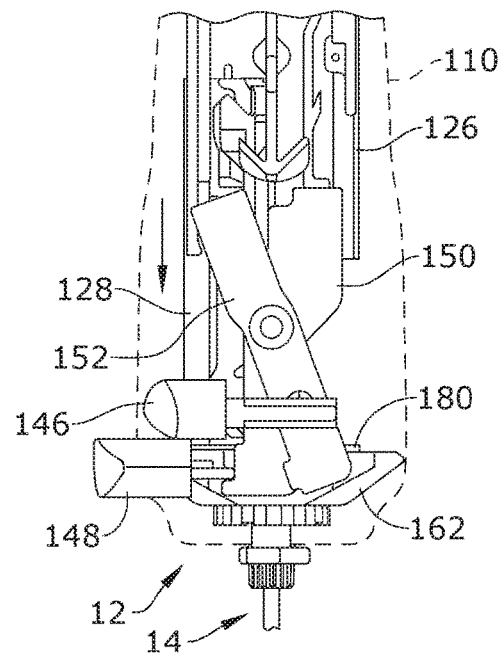
Figure 26:
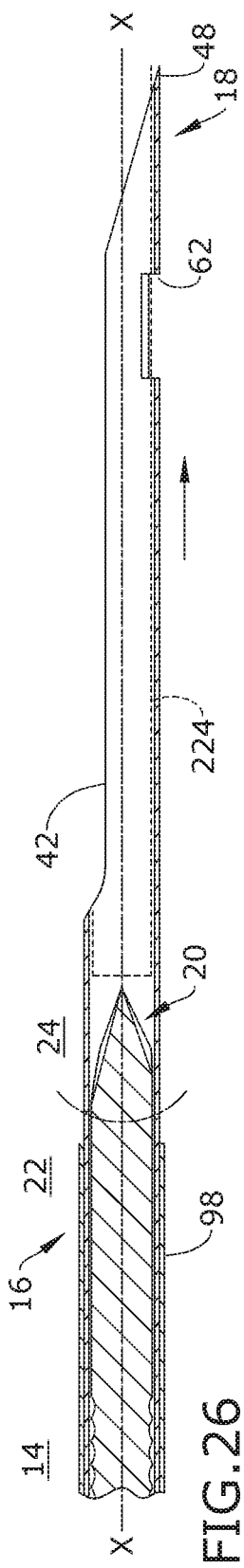

Operating the actuator assembly 12 for semi-automatic firing comprises a two-step actuating operation. The first button 146 is pressed inward as shown in FIG. 18, which causes the spoon cannula retainer 152 to pivot out of engagement with the catch 140, thereby releasing the spoon cannula carriage 128 to move distally as shown in FIG. 19, until it strikes the throw stop 162, or the optional damper 180, and causing the spoon cannula 18 to be fired into the lesion 24 over the stylet 20, as shown in FIG. 26. The spoon cannula 18 is axially advanced relative to the stylet 20 and the coring cannula 16 a distance predetermined by the sample size control assembly 116. In this intermediate position, a tissue specimen or a biopsy sample 224 begins to be cored by the spoon cannula 18 but still remains attached to the surrounding tissue, for example at one end and along the top and sides.

The needle configuration shown in FIG. 26 can be either a static or dynamic configuration. It is preferred that this is a dynamic configuration that the needle assembly 14 moves through as part of the overall movement of the needle assembly 14 from the armed configuration to the excising configuration, rather than a static configuration at which the overall movement of the needle assembly 14 pauses.

Figure 20:
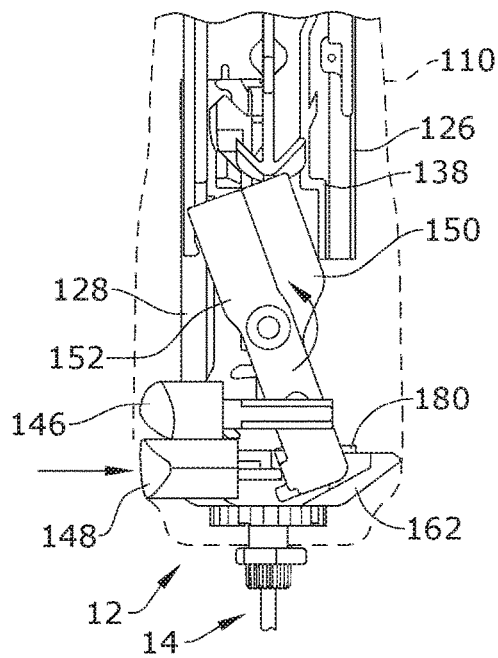
Figure 21:
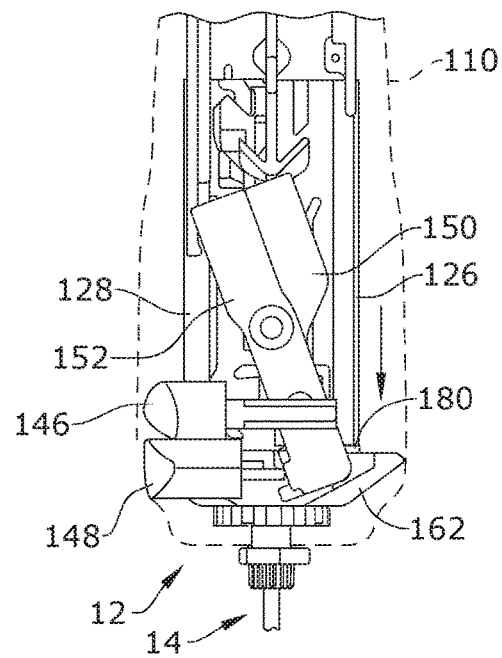
Figure 27:
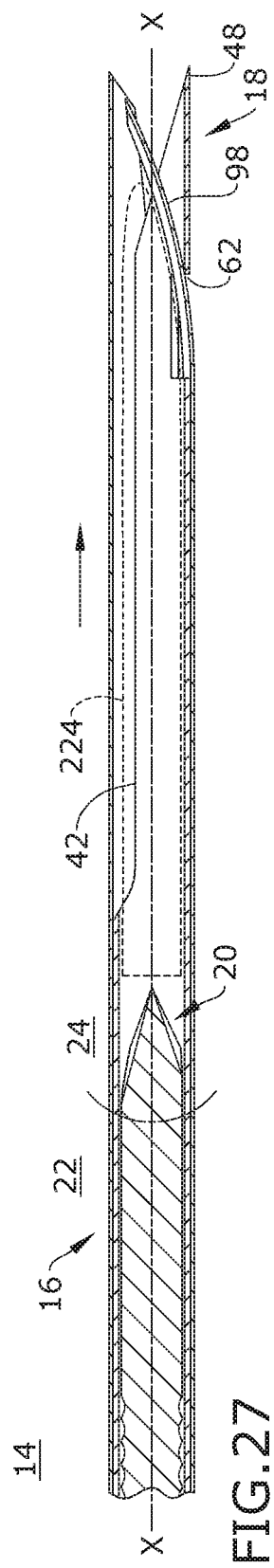

Subsequently, the second button 148 is pressed inward as shown in FIG. 20, which causes the coring cannula retainer 150 to pivot out of engagement with the catch 138, thereby releasing the coring cannula carriage 126 to move distally under influence of the spring 132 as shown in FIG. 21, until it strikes the throw stop 162, or the optional damper 180, and causing the coring cannula 16 to be fired into the lesion 24 over the spoon cannula 18 and the stylet 20, as shown in FIG. 27. The axial advancement of the coring cannula 16 to the excising position completes the coring of a biopsy sample 224. The cutting tip 92 completes coring along the top and sides of the biopsy sample 224. Also, the excising finger 98 extends through the window 62 in the spoon 42 and into the end of the sample 224. As the excising finger 98 reaches the open window 62, the inherent resilience and memory of the excising finger 98 causes it to resiliently return to its at-rest arcuate position, biased in the lesion 24 toward or crossing the longitudinal axis X, thereby severing or completely excising the biopsy sample 224 from the surrounding tissue.

In the present embodiment, because the biopsy sample 224 has already been partially cored by the spoon cannula 18 before the excising finger 98 reaches the window 62, the tissue is essentially stationary, or non-moving, relative to the excising finger 98 as the excising finger 98 extends through the open window 62. This can be beneficial in that the non-moving tissue urges the excising finger 98 even more into the pre-formed, at-rest arcuate position.

After excising the biopsy sample 224 from the lesion 24, the biopsy sample 224, which may be substantially cylindrical or bullet-shaped, will be held in place between the arcuate wall 90 and the radially-inward position of the excising finger 98. With this configuration, the sample 224 is retained within the coring cannula 16 upon removal from the tissue mass 22 by withdrawing the needle assembly.

This semi-automatic firing procedure provides the user with the ability to reposition the core biopsy device 10 if need be after the firing of the spoon cannula 18. For example, the user may fire the spoon cannula 18, confirm that the spoon 42 is in the desired location within the tissue mass 22 by some imaging technique, such as ultrasound, and then fire the coring cannula 16 to sever a biopsy sample from the tissue mass 22.

Operating the actuator assembly 12 for automatic firing comprises a one-step actuating operation. Without having initially pressed the first button 146, the second button 148 is pressed inward, as shown in FIG. 20. The second button 148 will contact the coring cannula retainer 150 and the spoon cannula retainer 152 substantially simultaneously, which causes the retainers 150, 152 to pivot out of engagement with the catches 138, 140 and release the cannula carriages 126, 128. The coring cannula carriage 126 is delayed by the delay arm 212 (FIGS. 12-13) while the spoon cannula carriage 128 is free to move distally under influence of the spring 134 until it strikes the throw stop 162, or the optional damper 180, and causing the spoon cannula 18 to be fired into the lesion 24 over the stylet 20 as described for FIG. 26.

The delay arm 212 is configured to delay the movement of the coring cannula carriage 126 for a predetermined period of time while the spoon cannula carriage 128 advances. After the release of the coring cannula carriage 126 by the retainer 150, the coring cannula carriage 126 is biased by the spring 132 to move distally, but is delayed by the projection 216 in front of the distal face of the carriage 126, as shown in FIG. 12. The continued distal movement of the coring cannula carriage 126 causes the delay arm 212 to pivot out of the way and allow the coring cannula carriage 126 to complete its distal movement, causing the coring cannula 16 to be fired into the lesion 24 over the spoon cannula 18 and the stylet 20 as described for FIG. 27.

The delay arm 212 reliably and correctly times the advancement of the coring cannula 16 over the spoon cannula 18. The delay arm 212 can be timed to delay movement of the coring cannula carriage 126 until the spoon cannula carriage 128 can completed it full range of movement.

The automatic firing procedure provides the user with the ability to quickly sever the biopsy sample from the tissue mass 22. This method enhances the likelihood that the needle assembly 14 will not move within the tissue mass 22 before the severing of the biopsy sample.

Figure 28:
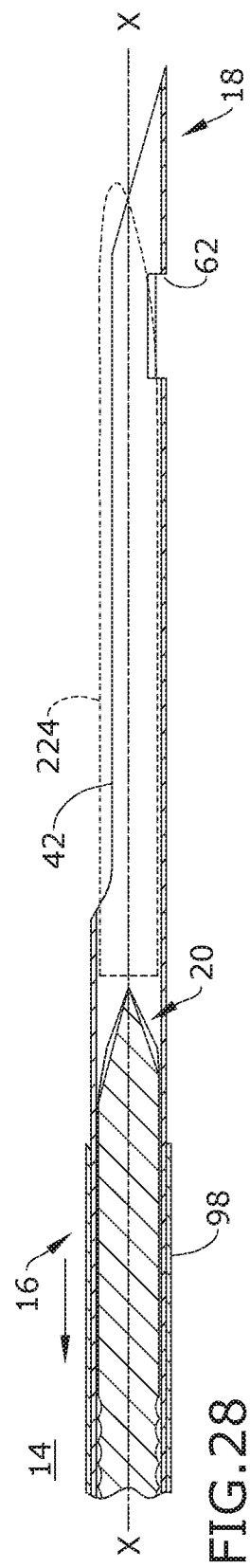

After a biopsy sample has been obtained, the needle assembly 14 is removed from the tissue mass 22 and the biopsy sample is collected. At this point, the core biopsy device 10 is in the unarmed or fired position. To collect the biopsy sample, a first arming stroke is performed by pulling the arming element 122 rearwardly or proximally once to retract the coring cannula 16 relative to the spoon cannula 18, which remains stationary. As shown in FIG. 28, after retracting the coring cannula 16, the excised biopsy sample 224 is supported on the spoon 42. The exposed biopsy sample 224 can then be retrieved or lifted from the spoon 42. This is an advantage over prior art biopsy devices that use the advancement of a stylet to expel the sample. The forced expulsion of the sample can damage the sample and in some cases can render the sample unusable.

If there is a need to fully re-arm the core biopsy device 10, such as to take multiple biopsy samples from the tissue mass 22, a second arming stroke readies the core biopsy device 10 for re-firing.

As briefly discussed above, the core biopsy device 10 can be a disposable medical device intended for use in obtaining one or more biopsy samples from one tissue mass 22. In this case, the needle assembly 14 may be effectively permanently coupled with the actuator assembly 12, as the entire device 10, including the actuator assembly 12 and needle assembly 14 may be disposed of after use. Alternatively, at least a portion of the core biopsy device 10 can be configured for reuse during more than one medical procedure. For example, the device 10 can have a reusable actuator assembly 12, and the needle assembly 14 can be a disposed of and replaced after each use. In this case, the needle assembly 14 may be removably coupled with the actuator assembly 12, and the actuator assembly 12 can be configured to be openable or otherwise accessible to remove a used needle assembly 14 and receive a new needle assembly 14. The actuator assembly 12, and any other portion of the core biopsy device 10 configured for reuse, can be sterilized.

FIGS. 29-30 show an alternative embodiment of the spoon cannula 18'. The spoon cannula 18' is substantially similar to the spoon cannula 18 shown in the previous figures, and like elements will be used to identify the same reference numerals bearing a prime (') symbol. The spoon cannula 18' differs in that the window 62' is rounded in shape. The window 62' as shown herein is a rounded rectangular opening in the arcuate wall 46' comprising a pair of parallel, spaced-apart longitudinal window edges 226 defining a window width 228 and joined by a proximal lateral window edge 230 and a distal lateral window edge 232 adjacent the insertion tip 48'. The longitudinal window edges 226 may lie substantially parallel to the axis X, and may be longer than lateral window edges 230, 232. The lateral window edges 230, 232 may lie substantially perpendicular to the axis X, and may be joined with the longitudinal window edges 226 by rounded convex corners 234. Further, the window 62' may be diametrically opposed to an open top of the spoon 42' defined by the longitudinal spoon edges 58'. Window shapes with radiused corners, such as the window 62' shown herein, add strength to the opening, and lower stress at the opening. Other shapes for the window 62' include rounded square, stadium, oval, circle, ellipse, or rectellipse.

The spoon cannula 18' may also have a low-profile spoon 42', in that the arcuate wall 46' may be shallower than the arcuate wall 46 of the embodiment shown in the previous figures. In one embodiment, the arcuate wall 46' can comprise an arc length defining a central angle ranging between about 120° and somewhat less than 180°.

FIG. 31 a cross-sectional view of a distal end of a needle assembly 14 assembled with the spoon cannula 18' of FIGS. 29-30. The needle assembly 14 is assembled by installing the stylet 20 into the lumen 56' of the spoon cannula 18', and installing the spoon cannula 18' into the lumen 86 of the coring cannula 16, to provide a telescoping assembly wherein the coring cannula 16 is slidably and coaxially disposed around the spoon cannula 18', which is slidably and coaxially disposed around the stylet 20. The excising finger 98 is adapted for slidable insertion through the window 62' in the spoon 42', as described above for the embodiment of FIG. 9. As the coring cannula 16 is advanced axially over the spoon cannula 18', the finger 98 will resiliently return to its at-rest position as it reaches the window 62'. The excising finger 98 will completely excise a biopsy sample when the finger 98 is extended through the window 62'. In this position, the insertion tip 48' and cutting tip 92 of the cannulas may be substantially aligned.

The needle assembly 14 shown in FIG. 31 can be operably attached to the actuator assembly 12 for operation as described previously herein. The needle assembly 14 shown in FIG. 31 can alternatively be operably attached to an actuator assembly of any suitable construction as long as it can axially extend or translate at least the coring and spoon cannulas 16, 18' in a controlled manner to ultimately place the coring cannula 16 in the excising position shown in FIG. 31, and ensure the separation of a biopsy sample from the tissue mass upon withdrawal of the needle assembly 14 from the tissue mass.

Figure 32:
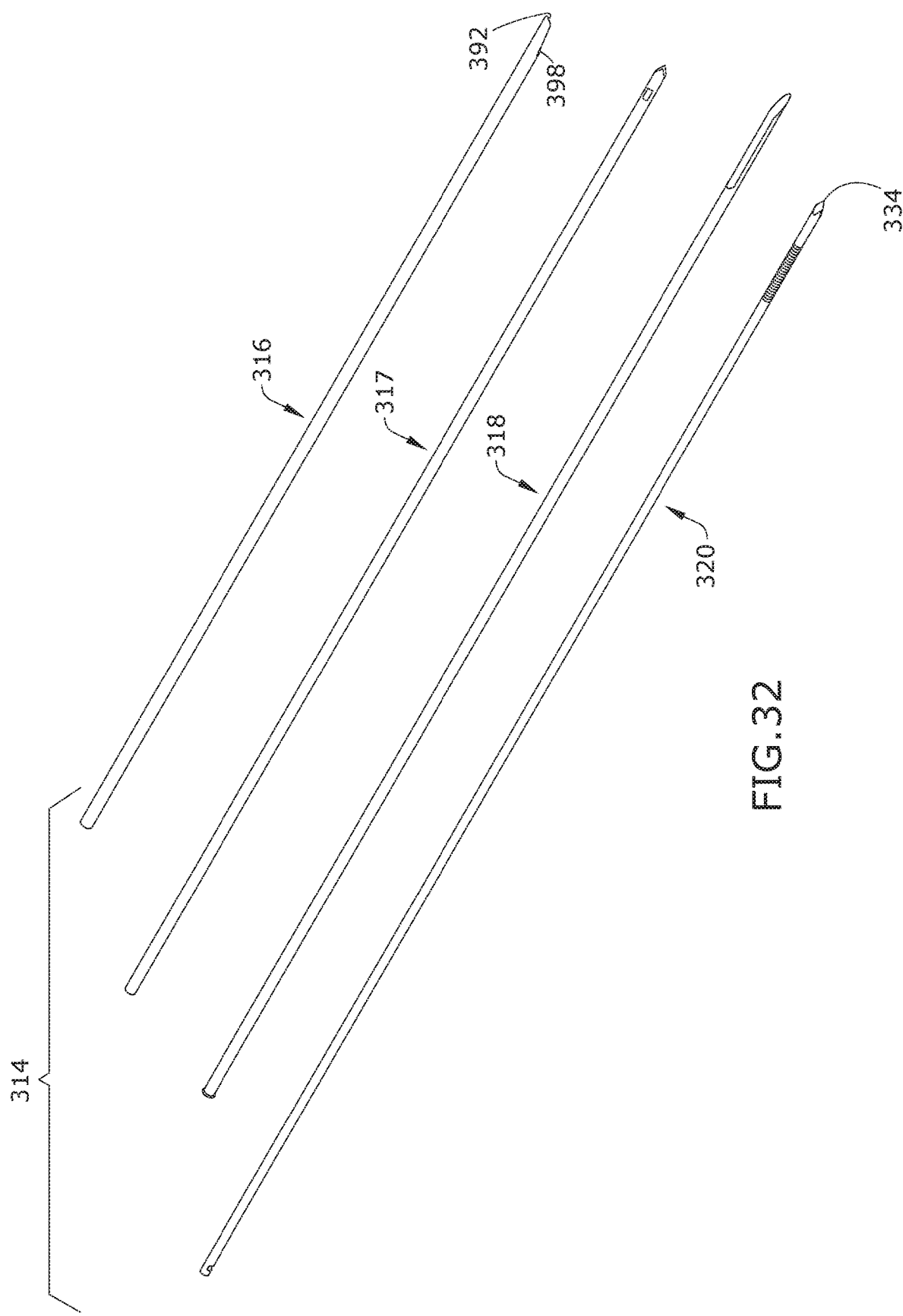
FIG. 32 is an exploded view of yet another alternative of the needle assembly of the full core biopsy device from FIG. 1.

FIG. 32 illustrates an exploded view of a needle assembly 314 that is substantially similar to the needle assembly 14. Therefore, like parts will be identified with like numerals increased by 300, with it being understood that the description of the like parts of the needle assembly 14 applies to the needle assembly 314 unless otherwise noted. The needle assembly 314 includes a first coring cannula, a second coring cannula, a spoon cannula 318, and a stylet 320 in coaxially telescoping relationship. By way of non-limiting example, the first and second coring cannulas can be an outer coring cannula 316 and an inner coring cannula 317. Preferably, the outer coring cannula 316, the inner coring cannula 317, the spoon cannula 318, and the stylet 320 are fabricated of a well-known surgically suitable material, such as stainless steel. At least a portion of the outer coring cannula 316, the inner coring cannula 317, the spoon cannula 318, and the stylet 320 can be made from material, shaped or provided with markings that enhance the visibility of the elements with an imaging system including, but not limited to radiography, ultrasound, or MRI.

The outer coring cannula 316 can be a similar structure to that illustrated in FIG. 6. The outer coring cannula 316 can include a cutting tip 392 and an excising finger 398. Similarly, the stylet 320 can be a similar structure to that illustrated in FIG. 3 and include a penetration tip 334.

FIG. 33 illustrates the spoon cannula 318 as an elongated, tubular member having an enclosed section 340 smoothly transitioning distally to a spoon 342 having an insertion tip 348. The enclosed section 340 comprises an annular wall 344 having an outer diameter 352 defining a lumen 356 having an inner diameter 354. The spoon 342 comprises an arcuate wall 346 contiguous with a portion of the annular wall 344. The maximum outer diameter and the maximum inner diameter of the spoon 342 can be the same as the outer diameter 352 and the inner diameter 354 of the enclosed section 340. The inner diameter 354 is greater than the maximum stylet diameter so that the stylet 320 can be slidably received within the lumen 356 and so that the spoon cannula 318 and stylet 320 can move axially relative to each other, i.e. translate along the axis X.

While the overall structure of the spoon cannula 318 can be similar to the spoon cannula 18 or the spoon cannula 18', the spoon cannula 318 does not include a window. The absence of a window in the spoon cannula 318 can provide additional support for the tissue sample.

Referring to FIGS. 34-35, the inner coring cannula 317 is an elongated, tubular member having an enclosed section 381 which transitions distally to a cutting section 383. The enclosed section 381 comprises an annular wall 385 defining a lumen 387 having an inner diameter 389. The inner diameter 389 of the inner coring cannula 317 is somewhat greater than the outer diameter 352 of the spoon cannula 318 so that the spoon cannula 318 can be slidably received within the lumen 387 of the inner coring cannula 317 and so that the inner coring cannula 317 and the spoon cannula 318 can move axially relative to each other, i.e. translate along the axis X.

The inner coring cannula 317 has an outer diameter 391 that is slightly less than the inner diameter of the outer coring cannula 316, allowing the inner coring cannula 317 to be slidably received within the outer coring cannula 316. The outer coring cannula 316, the inner coring cannula 317, the spoon cannula 318, and the stylet 320 can move axially relative to each other, i.e. translate along the axis X.

The cutting section 383 comprises at least one cutting edge or tip 393. The at least one cutting edge or tip 393 can have various tip shapes, including, but not limited to, Franseen type (as shown), beveled, diamond, serrated, conical, or chamfered.

The inner coring cannula 317 is provided with a slot or window 362 adjacent the cutting section 383. The window 362 as shown herein by way of non-limiting example is a generally rectilinear opening in the annular wall 385. Alternatively, the window 362 can have shapes such as, but is not limited to, substantially a circle, a rounded rectangle, a triangle, or a square. The location of the window 362 on the inner coring cannula 317 is in contrast to the location of the window on the spoon cannula 18 or 18'.

The operation of the needle assembly 314 will be described with respect to FIG. 36-39. Any suitable actuator, fully-automatic, fully-manual, or a combination automatic and manual can be used to sequentially move the cannulas 318, 317, 316. For example, the actuator of FIGS. 10-21 can easily be modified to accommodate three cannulas, instead of the illustrated two. It is further considered that the stylet 320 can be stationary within the cannulas 318, 317, 316 or able to move relative to the cannulas 318, 317, 316 along the axis X.

Figure 36:
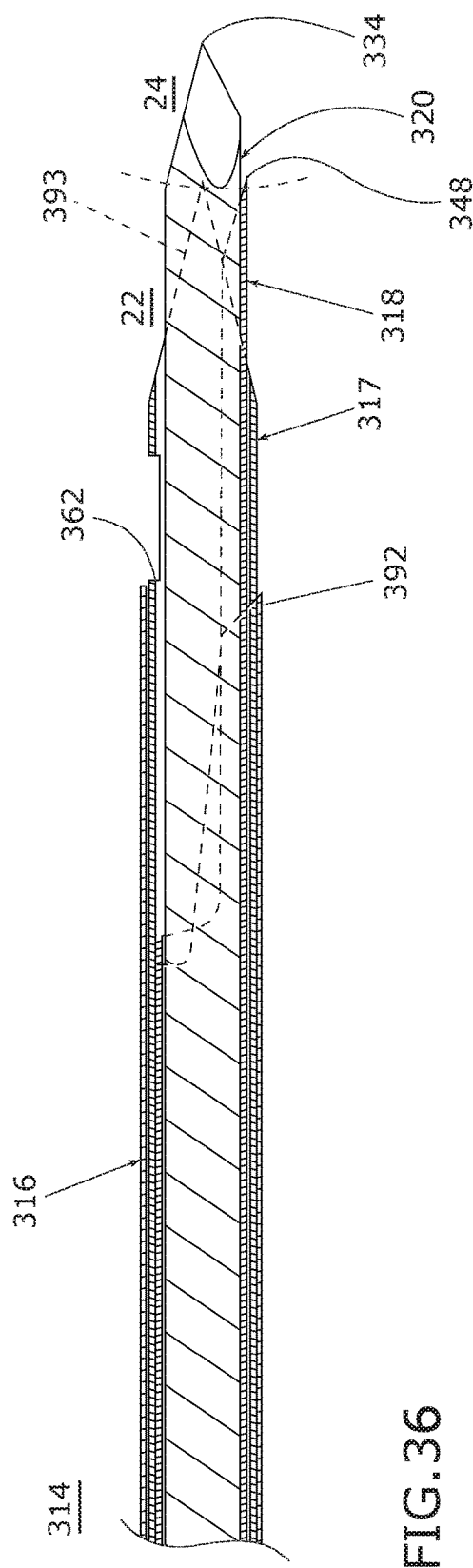
FIGS. 36-39 are longitudinal sectional views of the needle assembly at various steps in the process of obtaining a core biopsy sample.

Turning to the operation, FIG. 36 illustrates the needle assembly 314 in the fully armed position and the biopsy sample size optionally set as desired. The needle assembly 314 is inserted into the tissue mass 22 so that the penetration tip 334 of the stylet 320 is adjacent to or within the target area or lesion 24. The penetration tip 334 of the stylet 320 can extend somewhat distally of the tips 348, 393, 392, of the cannulas 318, 317, 316 to form a generally solid penetrating tip that facilitates the insertion of the needle assembly 314 into the tissue mass 22. The needle assembly 314 can optionally be guided during insertion using an imaging system. Any suitable imaging system can be used, for example radiography, ultrasound, or MRI.

Figure 37:
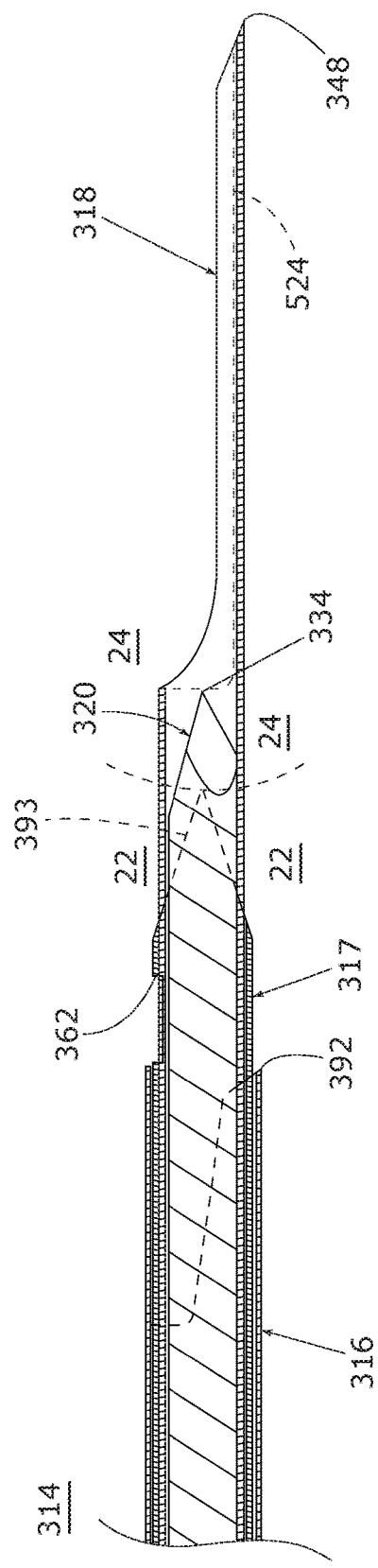

FIG. 37 illustrates the distal deployment of the spoon cannula 318 into the lesion 24 to partially form a full-core specimen 524. The insertion tip 348 initiates the coring of the full-core specimen 524 similarly to FIG. 26. In this intermediate position, the full-core specimen 524 begins to be cored by the spoon cannula 318 but still remains attached to the surrounding tissue, for example at one end and along the top and sides.

Figure 38:
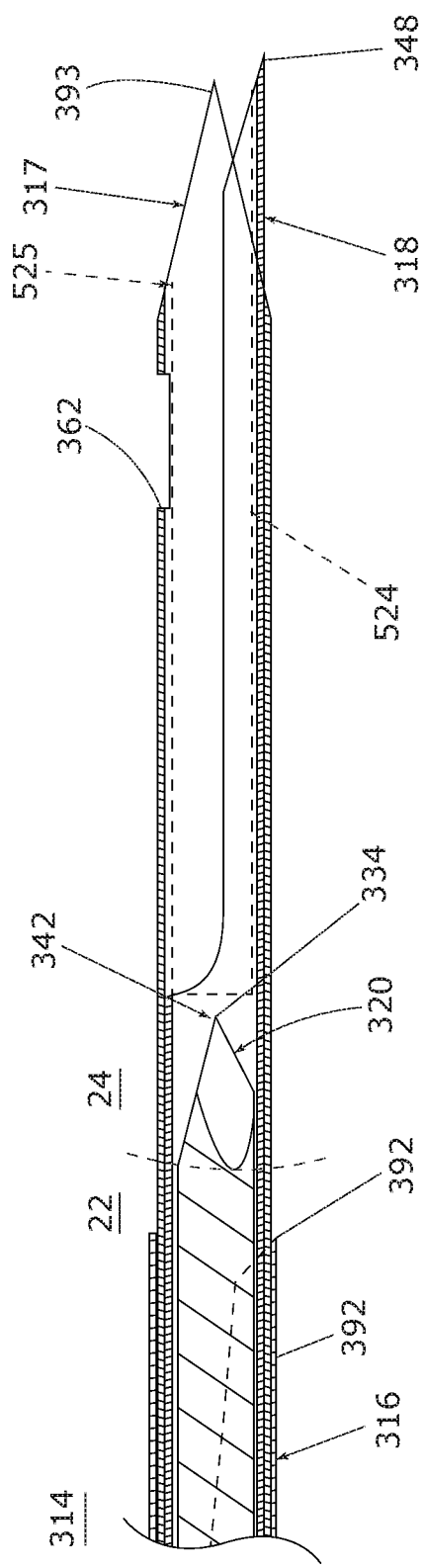

FIG. 38 illustrates the distal deployment of the inner coring cannula 317. The motion of the inner coring cannula 317 can result in further coring of the full-core specimen 524. For example, the top and side portions of the full-core specimen 524 can be separated from the surrounding tissue, leaving a distal end 525 of the full-core specimen 524 still attached to the lesion 24. In this non-limiting example, at the completion of the distal motion of the inner coring cannula 317, the window 362 in the annular wall 385 is positioned above the spoon 342 adjacent the insertion tip 348.

Figure 39:
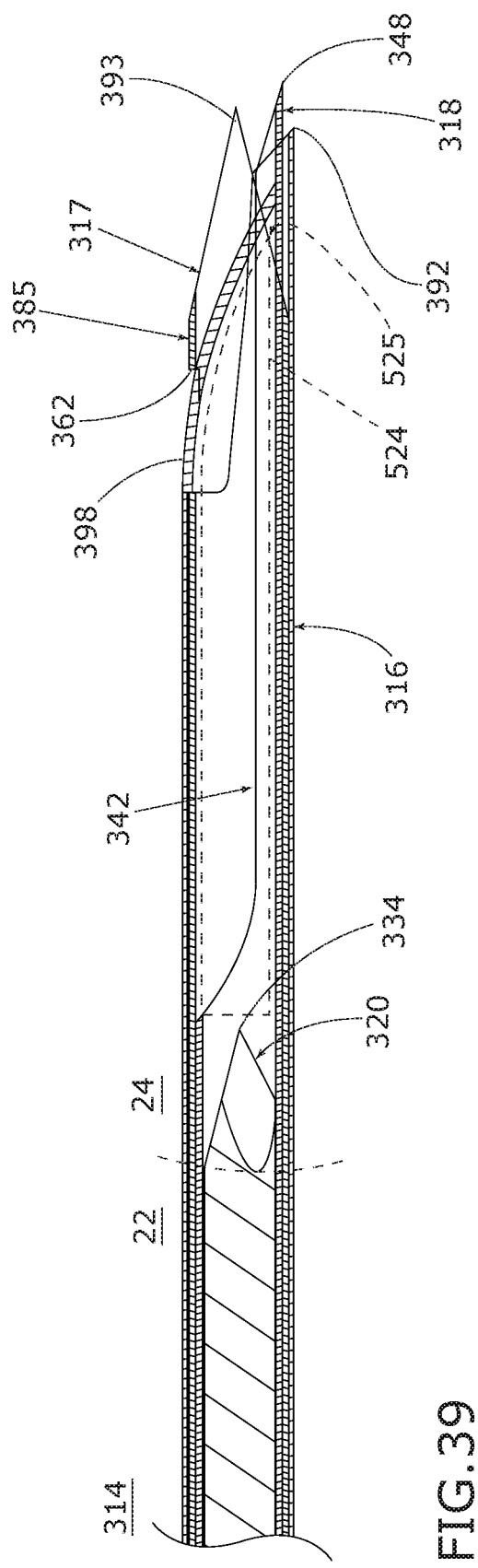

FIG. 39 illustrates the distal deployment of the outer coring cannula 316. The excising finger 398 of the outer coring cannula 316 extends through the window 362 in the inner coring cannula 317. As the excising finger 398 reaches the open window 362, the inherent resilience and memory of the excising finger 398 causes it to resiliently return to its at-rest arcuate position, biased in the lesion 24 toward or crossing the longitudinal axis X, thereby severing or completely excising the biopsy sample from the surrounding tissue. By way of non-limiting example, the excising finger 398 can biased toward a portion of the spoon 342 adjacent the insertion tip 348 to sever the distal end 525 of the full-core specimen 524.

Figure 40:
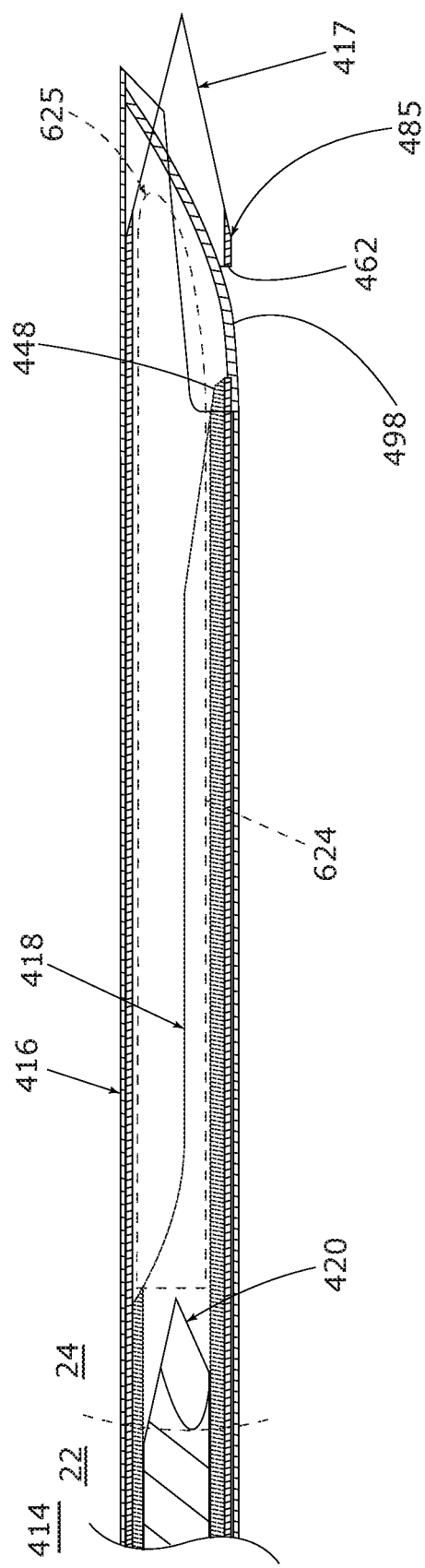
FIG. 40 is an alternative embodiment of the needle assemble of FIG. 32.

FIG. 40 illustrates a needle assembly 414 that is substantially similar to the needle assembly 314. Therefore, like parts will be identified with like numerals increased by 100, with it being understood that the description of the like parts of the needle assembly 314 applies to the needle assembly 414 unless otherwise noted. The needle assembly 414 comprises an outer coring cannula 416, an inner coring cannula 417, a spoon cannula 418, and a stylet 420 in coaxially telescoping relationship. At the completion of the distal motion of the needle assembly 414, a window 462 in the annular wall 485 is positioned beneath and distally beyond an insertion tip 448. An excising finger 498 can complete the coring of a full-core specimen 624. By way of non-limiting example, the excising finger 498 can be biased toward a portion of the outer coring cannula 416, severing the distal end 625 of the full-core specimen 624. Severing or completely excising the full-core specimen 624 at a position distal of the spoon cannula 418 allows for a larger full-core specimen. It is contemplated that different arrangements of the elements of the needle assemblies 314, 414 can result in variety of sizes of full-core specimens.

To the extent not already described, the different features and structures of the various embodiments of the core biopsy device 10 may be used in combination with each other as desired. That one feature may not be illustrated in all of the embodiments of the tub assemblies core biopsy device 10 is not meant to be construed that it cannot be, but is done for brevity of description. In particular, the needle assembly 14 may be used with other actuator assemblies not illustrated herein. Thus, the various features of the different embodiments of the core biopsy device 10 may be mixed and matched as desired to form new embodiments, whether or not the new embodiments are expressly described.

There are several advantages of the present disclosure arising from the various features of the apparatus, systems, and methods described herein. For example, the embodiments of the invention described above provides a full core biopsy device with an outer coring cannula with a finger on the distal end thereof and an inner spoon cannula with a spoon on the distal end thereof. A window or slot is provided in the spoon. The finger is configured to prolapse through the window into a lumen of the inner spoon cannula to sever a tissue sample upon translation or axial advancement of the outer coring cannula over the inner spoon cannula.

Another advantage of some embodiments of the present disclosure is that the spoon enables the biopsy sample to be removed from the device without disturbance of the sample. Previous devices have used a cutting finger on an outer cannula, but when fired the inner and outer cannulas fire forward simultaneously, with the outer cannula continuing its travel a few milimeters more so the cutting finger protrudes through a window on the inner cannula to sever tissue. Such devices have required the inner cannula to be shaped like a tube so that when fired, the inner cannula severs tissue in a complete 360 degree circle corresponding to the circumference of the cannula as it moves through the tissue. When the cutting finger extends through the window, it completely severs the tissue inside the inner cannula and keeps the tissue wholly inside the inner cannula.

Another advantage of some embodiments of the present disclosure is that a complete biopsy sample can be excised from the surrounding tissue without requiring rotation of any of the components of the needle assembly, which can add to the complexity and cost of the biopsy device.

Yet another advantage of some embodiments of the present disclosure is that the core biopsy device minimizes patient discomfort and insures a complete excision of the biopsy sample from the surrounding tissue.

While the invention has been specifically described in connection with certain specific embodiments thereof, it is to be understood that this is by way of illustration and not of limitation. Reasonable variation and modification are possible with the scope of the foregoing disclosure and drawings without departing from the spirit of the invention which, is defined in the appended claims. Hence, specific dimensions and other physical characteristics relating to the embodiments disclosed herein are not to be considered as limiting, unless the claims expressly state otherwise.

What is claimed is:

1. A biopsy device comprising:
an operationally stationary stylet terminating in a penetration tip;
a spoon cannula having an annular wall forming an enclosed section defining a first lumen in which the stylet is received, and a spoon having a first arcuate wall contiguous with and extending from a portion of the annular wall, the first arcuate wall having spaced first edges defining a specimen opening and terminating in a spoon tip, and a window is located in the first arcuate wall;
a coring cannula having an enclosed section defining a second lumen in which the spoon cannula is received, and a cutting section extending distally from the enclosed section, the cutting section having a second arcuate wall having spaced second edges and terminating in a coring tip, and with an excising finger radially spaced from and longitudinally overlapping the second arcuate wall; and
an actuator assembly operably coupled to the spoon cannula and the coring cannula to effect movement of the spoon cannula and coring cannula from an armed position to a fired position to take a tissue specimen from a tissue mass, in the armed position, at least the stylet and spoon are arranged such that the stylet resides within the spoon, in the fired position, the stylet, spoon and cutting section are arranged such that the spoon extends beyond the penetration tip of the stylet, the second arcuate wall closes at least a portion of the specimen opening, and the excising finger extends through the window.

2. The biopsy device of claim 1 further comprising a sample size control assembly.

3. The biopsy device of claim 2 wherein the sample size control assembly comprises an adjuster member and a throw stop coupled to the adjuster member.

4. The biopsy device of claim 3 wherein the adjuster member comprises a screw-shaped threaded body and the throw stop threadably mounted to the screw-shaped threaded body for linear movement along the screw-shaped threaded body.

5. The biopsy device of claim 4 wherein the sample size control assembly further comprises an actuator coupled to the screw-shaped threaded body.

6. The biopsy device of claim 1 wherein the first arcuate wall has an arc length defining a central angle of greater than or equal to 120 degrees.

7. The biopsy device of claim 6 wherein the first arcuate wall has an arc length defining a central angle of less than or equal to 180 degrees.

8. The biopsy device of claim 1 wherein the second arcuate wall has an arc length defining a central angle of greater than or equal to 120 degrees.

9. The biopsy device of claim 8 wherein the second arcuate wall has an arc length defining a central angle of less than or equal to 180 degrees.

10. The biopsy device of claim 1 wherein the spoon tip is beveled.

11. The biopsy device of claim 1 wherein the spaced first edges of the spoon are beveled.

12. The biopsy device of claim 1 wherein the coring tip is beveled.

13. The biopsy device of claim 1 wherein the spaced second edges of the cutting section are beveled.

14. The biopsy device of claim 1 wherein the excising finger is opposite the second arcuate wall.

15. The biopsy device of claim 1 wherein the excising finger is resilient.

16. The biopsy device of claim 1 wherein the excising finger is of a length that in the fired position, the excising finger extends beyond a centerline of the spoon cannula.

17. The biopsy device of claim 16 wherein the excising finger is of a length that in the fired position, the excising finger extends to the second arcuate wall.

18. The biopsy device of claim 1 wherein:
the first arcuate wall has an arc length defining a central angle of greater than or equal to 120 degrees and less than or equal to 180 degrees;
the second arcuate wall has an arc length defining a central angle of greater than or equal to 120 degrees and less than or equal to 180 degrees;
the spoon tip, first edges, coring tip, and second edges are beveled; and
the excising finger is resilient and opposite the second arcuate wall and has a biased position where a tip of the excising finger is adjacent the second arcuate wall.

19. The biopsy device of claim 1 wherein the excising finger is opposite the second arcuate wall and has a biased position where a tip of the excising finger is adjacent the second arcuate wall.

20. A biopsy device comprising:
a stylet terminating in a penetration tip;
a spoon cannula having an annular wall forming an enclosed section defining a spoon lumen in which the stylet is received, and a spoon having a spoon arcuate wall contiguous with and extending from a portion of the annular wall, the spoon arcuate wall having spaced spoon edges defining a specimen opening and terminating in a spoon tip;
a first coring cannula defining a first coring cannula lumen and terminating in a first coring tip;
a second coring cannula defining a second coring cannula lumen and terminating in a second coring tip, with the spoon cannula, first coring cannula, and second coring all coaxially arranged;
a window located in one of the first and second coring cannulas;
an excising finger extending from another one of the first and second coring cannulas, wherein the excising finger is radially spaced from and longitudinally overlapping a coring cannula arcuate wall; and
an actuator assembly operably coupled to the stylet, spoon cannula, first coring cannula and second coring cannula to effect movement of the spoon cannula, first coring cannula, and second coring cannula from an armed position to a fired position to take a tissue specimen from a tissue mass, in the armed position, at least the penetration tip extends beyond the spoon tip, and, in the fired position, the spoon tip extends beyond the penetration tip, at least one of the first and second coring cannulas closes a portion of the specimen opening, and the excising finger extends through the window.

21. The biopsy device of claim 20 further comprising a sample size control assembly.

22. The biopsy device of claim 21 wherein the sample size control assembly comprises an adjuster member and a throw stop coupled to the adjuster member.

23. The biopsy device of claim 22 wherein the adjuster member comprises a screw-shaped threaded body and the throw stop threadably mounted to the screw-shaped threaded body for linear movement along the screw-shaped threaded body.

24. The biopsy device of claim 23 wherein the sample size control assembly further comprises an actuator coupled to the screw-shaped threaded body.

25. The biopsy device of claim 20 wherein at least one of the spoon arcuate wall or first coring cannula arcuate wall has an arc length defining a central angle of greater than or equal to 120 degrees.

26. The biopsy device of claim 20 wherein the at least one of the spoon arcuate wall or first coring cannula arcuate wall has an arc length defining a central angle of less than or equal to 180 degrees.

27. The biopsy device of claim 20 wherein at least one of the spoon tip, the first coring tip, or the second coring tip is beveled.

28. The biopsy device of claim 20 wherein at least one of the spaced spoon edges are beveled.

29. The biopsy device of claim 20 wherein the excising finger is opposite the specimen opening.

30. The biopsy device of claim 20 wherein the excising finger is resilient.

31. The biopsy device of claim 20 wherein the excising finger is of a length that in the fired position, the excising finger extends beyond a centerline of the spoon cannula.

32. The biopsy device of claim 20 wherein the spoon is received within the first coring cannula lumen and the first coring cannula is received within the second coring cannula lumen.

33. The biopsy device of claim 32 wherein the window is located on the first coring cannula and the excising finger is located on the second coring cannula.

34. A biopsy device comprising:
a stylet terminating in a penetration tip;
a spoon cannula having an annular wall forming an enclosed section defining a first lumen in which the stylet is received, and a spoon having a first arcuate wall contiguous with and extending from a portion of the annular wall, the first arcuate wall having spaced first edges defining a specimen opening and terminating in a spoon tip, and a window is located in the first arcuate wall;
a coring cannula having an enclosed section defining a second lumen in which the spoon cannula is received, and a cutting section extending distally from the enclosed section, the cutting section having a second arcuate wall having spaced second edges and terminating in a coring tip, and with an excising finger radially spaced from and longitudinally overlapping the second arcuate wall; and
an actuator assembly operably coupled to the spoon cannula and the coring cannula to effect movement of the spoon cannula and coring cannula from an armed position to a fired position in which the excising finger extends through the window toward the second arcuate wall.

35. The biopsy device of claim 34 wherein the first arcuate wall has an arc length defining a central angle of greater than or equal to 120 degrees.

36. The biopsy device of claim 34 wherein the first arcuate wall has an arc length defining a central angle of less than or equal to 180 degrees.

37. The biopsy device of claim 34 wherein the window is a rectilinear opening comprising a pair of parallel, spaced-apart longitudinal window edges defining a window width and joined by a proximal lateral window edge and a distal lateral window edge adjacent the spoon tip.

38. The biopsy device of claim 37 wherein the spaced-apart longitudinal window edges are longer than the proximal lateral window edge and the distal lateral window edge.

39. The biopsy device of claim 34 wherein the spoon tip is beveled.

40. The biopsy device of claim 34 wherein the spaced first edges of the spoon are beveled.

41. The biopsy device of claim 34 wherein the coring tip is beveled.

42. The biopsy device of claim 34 wherein the spaced second edges of the cutting section are beveled.

43. The biopsy device of claim 34 wherein the excising finger is of a length that in the fired position, the excising finger extends beyond a centerline of the spoon cannula.

\* \* \* \* \*